US008579897B2

(12) United States Patent
Vakharia et al.

(10) Patent No.: US 8,579,897 B2
(45) Date of Patent: *Nov. 12, 2013

(54) BIPOLAR FORCEPS

(75) Inventors: Omar J. Vakharia, Cincinnati, OH (US); Gary L. Long, Cincinnati, OH (US); Kurt R. Bally, Lebanon, OH (US); Andrew M. Zwolinski, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1204 days.

This patent is subject to a terminal disclaimer.

(21) Appl. No.: 11/986,489

(22) Filed: Nov. 21, 2007

(65) Prior Publication Data

US 2009/0131932 A1 May 21, 2009

(51) Int. Cl.
*A61B 18/14* (2006.01)
*A61B 17/28* (2006.01)

(52) U.S. Cl.
USPC .............................................. 606/52; 606/207

(58) Field of Classification Search
USPC ........................ 606/50–52, 205–207
See application file for complete search history.

(56) References Cited

U.S. PATENT DOCUMENTS

| 645,576 | A | 3/1900 | Telsa |
| 649,621 | A | 5/1900 | Tesla |
| 787,412 | A | 4/1905 | Tesla |
| 1,039,354 | A | 9/1912 | Bonadio |
| 1,127,948 | A | 2/1915 | Wappler |
| 1,482,653 | A | 2/1924 | Lilly |
| 1,625,602 | A | 4/1927 | Gould et al. |
| 1,916,722 | A | 7/1933 | Ende |
| 2,028,635 | A | 1/1936 | Wappler |
| 2,031,682 | A * | 2/1936 | Wappler et al. ................. 606/46 |
| 2,113,246 | A | 4/1938 | Wappler |
| 2,155,365 | A | 4/1939 | Rankin |
| 2,191,858 | A | 2/1940 | Moore |

(Continued)

FOREIGN PATENT DOCUMENTS

| AU | 666310 B2 | 2/1996 |
| DE | 3008120 A1 | 9/1980 |

(Continued)

OTHER PUBLICATIONS

International Search Report for PCT/US2008/084311, Jul. 10, 2009 (7 pages).

(Continued)

*Primary Examiner* — Ronald Hupczey, Jr.

(57) ABSTRACT

In various surgical techniques, a bipolar forceps can be used to seal a vessel in two locations such that the vessel can be incised at a location positioned intermediate the two seal locations. The bipolar forceps can include a cutting element which can be configured to incise the vessel. In various embodiments, the cutting element can include a sharp edge which can be moved relative to the vessel. In at least one embodiment, the cutting element can be electrically connected to a source of energy. The bipolar forceps can include first and second electrodes positioned within first and second jaw members, respectively, wherein at least one of the jaw members can include a substantially tapered profile and can be configured to pull the vessel away from the surrounding soft tissue. Such jaw members can include ridges, teeth, and/or a textured outer surface configured to grip the soft tissue and/or vessel.

6 Claims, 24 Drawing Sheets

(56) References Cited

U.S. PATENT DOCUMENTS

| | | |
|---|---|---|
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,423 A | 5/1994 | Rosenbluth et al. |
| 5,318,589 A * | 6/1994 | Lichtman ............... 606/205 |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |

(56) References Cited

U.S. PATENT DOCUMENTS

| | | |
|---|---|---|
| 5,334,198 A | 8/1994 | Hart et al. |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,499 A | 8/1995 | Fritzsch |
| 5,443,463 A * | 8/1995 | Stern et al. .................. 606/51 |
| 5,445,638 A * | 8/1995 | Rydell et al. ................ 606/51 |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A | 12/1995 | Fowler |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,601,602 A | 2/1997 | Fowler |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,728,094 A | 3/1998 | Edwards |

(56) References Cited

U.S. PATENT DOCUMENTS

| | | | |
|---|---|---|---|
| 5,730,740 | A | 3/1998 | Wales et al. |
| 5,735,849 | A * | 4/1998 | Baden et al. ............ 606/51 |
| 5,741,234 | A | 4/1998 | Aboul-Hosn |
| 5,741,278 | A | 4/1998 | Stevens |
| 5,741,285 | A | 4/1998 | McBrayer et al. |
| 5,741,429 | A | 4/1998 | Donadio, III et al. |
| 5,743,456 | A | 4/1998 | Jones et al. |
| 5,746,759 | A | 5/1998 | Meade et al. |
| 5,749,826 | A | 5/1998 | Faulkner |
| 5,749,881 | A | 5/1998 | Sackier et al. |
| 5,749,889 | A | 5/1998 | Bacich et al. |
| 5,752,951 | A | 5/1998 | Yanik |
| 5,755,731 | A | 5/1998 | Grinberg |
| 5,762,604 | A | 6/1998 | Kieturakis |
| 5,766,167 | A | 6/1998 | Eggers et al. |
| 5,766,170 | A | 6/1998 | Eggers |
| 5,766,205 | A | 6/1998 | Zvenyatsky et al. |
| 5,769,849 | A | 6/1998 | Eggers |
| 5,779,701 | A | 7/1998 | McBrayer et al. |
| 5,779,716 | A | 7/1998 | Cano et al. |
| 5,779,727 | A | 7/1998 | Orejola |
| 5,782,859 | A | 7/1998 | Nicholas et al. |
| 5,782,861 | A | 7/1998 | Cragg et al. |
| 5,782,866 | A | 7/1998 | Wenstrom, Jr. |
| 5,791,022 | A | 8/1998 | Bohman |
| 5,792,113 | A | 8/1998 | Kramer et al. |
| 5,792,153 | A | 8/1998 | Swain et al. |
| 5,792,165 | A | 8/1998 | Klieman et al. |
| 5,797,835 | A | 8/1998 | Green |
| 5,797,928 | A | 8/1998 | Kogasaka |
| 5,797,939 | A | 8/1998 | Yoon |
| 5,797,941 | A | 8/1998 | Schulze et al. |
| 5,797,959 | A | 8/1998 | Castro et al. |
| 5,803,903 | A | 9/1998 | Athas et al. |
| 5,808,665 | A | 9/1998 | Green |
| 5,810,806 | A | 9/1998 | Ritchart et al. |
| 5,810,849 | A | 9/1998 | Kontos |
| 5,810,865 | A | 9/1998 | Koscher et al. |
| 5,810,876 | A | 9/1998 | Kelleher |
| 5,810,877 | A | 9/1998 | Roth et al. |
| 5,813,976 | A | 9/1998 | Filipi et al. |
| 5,814,058 | A | 9/1998 | Carlson et al. |
| 5,817,061 | A | 10/1998 | Goodwin et al. |
| 5,817,107 | A | 10/1998 | Schaller |
| 5,817,119 | A | 10/1998 | Klieman et al. |
| 5,819,736 | A | 10/1998 | Avny et al. |
| 5,823,947 | A | 10/1998 | Yoon et al. |
| 5,824,071 | A | 10/1998 | Nelson et al. |
| 5,827,276 | A | 10/1998 | LeVeen et al. |
| 5,827,281 | A | 10/1998 | Levin |
| 5,827,299 | A | 10/1998 | Thomason et al. |
| 5,827,323 | A | 10/1998 | Klieman et al. |
| 5,830,231 | A | 11/1998 | Geiges, Jr. |
| 5,833,603 | A | 11/1998 | Kovacs et al. |
| 5,833,700 | A | 11/1998 | Fogelberg et al. |
| 5,833,703 | A | 11/1998 | Manushakian |
| 5,836,960 | A | 11/1998 | Kolesa et al. |
| 5,843,017 | A | 12/1998 | Yoon |
| 5,843,121 | A | 12/1998 | Yoon |
| 5,849,022 | A | 12/1998 | Sakashita et al. |
| 5,853,374 | A | 12/1998 | Hart et al. |
| 5,855,585 | A | 1/1999 | Kontos |
| 5,860,913 | A | 1/1999 | Yamaya et al. |
| 5,860,995 | A | 1/1999 | Berkelaar |
| 5,868,762 | A | 2/1999 | Cragg et al. |
| 5,876,411 | A | 3/1999 | Kontos |
| 5,882,331 | A | 3/1999 | Sasaki |
| 5,882,344 | A | 3/1999 | Stouder, Jr. |
| 5,893,846 | A | 4/1999 | Bales et al. |
| 5,893,874 | A | 4/1999 | Bourque et al. |
| 5,893,875 | A | 4/1999 | O'Connor et al. |
| 5,897,487 | A | 4/1999 | Ouchi |
| 5,899,919 | A | 5/1999 | Eubanks, Jr. et al. |
| 5,902,238 | A | 5/1999 | Golden et al. |
| 5,902,254 | A | 5/1999 | Magram |
| 5,904,702 | A | 5/1999 | Ek et al. |
| 5,908,420 | A | 6/1999 | Parins et al. |
| 5,908,429 | A | 6/1999 | Yoon |
| 5,911,737 | A | 6/1999 | Lee et al. |
| 5,916,146 | A | 6/1999 | Allotta et al. |
| 5,916,147 | A | 6/1999 | Boury |
| 5,921,993 | A | 7/1999 | Yoon |
| 5,921,997 | A | 7/1999 | Fogelberg et al. |
| 5,922,008 | A | 7/1999 | Gimpelson |
| 5,925,052 | A | 7/1999 | Simmons |
| 5,928,255 | A | 7/1999 | Meade et al. |
| 5,928,266 | A | 7/1999 | Kontos |
| 5,936,536 | A | 8/1999 | Morris |
| 5,944,718 | A | 8/1999 | Austin et al. |
| 5,951,547 | A | 9/1999 | Gough et al. |
| 5,951,549 | A | 9/1999 | Richardson et al. |
| 5,954,720 | A | 9/1999 | Wilson et al. |
| 5,954,731 | A | 9/1999 | Yoon |
| 5,957,936 | A | 9/1999 | Yoon et al. |
| 5,957,943 | A | 9/1999 | Vaitekunas |
| 5,957,953 | A | 9/1999 | DiPoto et al. |
| 5,964,782 | A | 10/1999 | Lafontaine et al. |
| 5,971,995 | A | 10/1999 | Rousseau |
| 5,972,002 | A | 10/1999 | Bark et al. |
| 5,976,074 | A | 11/1999 | Moriyama |
| 5,976,075 | A | 11/1999 | Beane et al. |
| 5,976,130 | A | 11/1999 | McBrayer et al. |
| 5,976,131 | A | 11/1999 | Guglielmi et al. |
| 5,980,539 | A | 11/1999 | Kontos |
| 5,980,556 | A | 11/1999 | Giordano et al. |
| 5,984,938 | A | 11/1999 | Yoon |
| 5,984,939 | A | 11/1999 | Yoon |
| 5,984,950 | A | 11/1999 | Cragg et al. |
| 5,989,182 | A | 11/1999 | Hori et al. |
| 5,993,447 | A | 11/1999 | Blewett et al. |
| 5,993,474 | A | 11/1999 | Ouchi |
| 5,995,875 | A | 11/1999 | Blewett et al. |
| 5,997,555 | A | 12/1999 | Kontos |
| 6,001,120 | A | 12/1999 | Levin |
| 6,004,269 | A | 12/1999 | Crowley et al. |
| 6,004,330 | A | 12/1999 | Middleman et al. |
| 6,007,566 | A | 12/1999 | Wenstrom, Jr. |
| 6,010,515 | A | 1/2000 | Swain et al. |
| 6,012,494 | A | 1/2000 | Balazs |
| 6,016,452 | A | 1/2000 | Kasevich |
| 6,017,356 | A | 1/2000 | Frederick et al. |
| 6,019,770 | A | 2/2000 | Christoudias |
| 6,024,708 | A | 2/2000 | Bales et al. |
| 6,024,747 | A | 2/2000 | Kontos |
| 6,027,522 | A | 2/2000 | Palmer |
| 6,030,365 | A | 2/2000 | Laufer |
| 6,030,384 | A | 2/2000 | Nezhat |
| 6,030,634 | A | 2/2000 | Wu et al. |
| 6,033,399 | A | 3/2000 | Gines |
| 6,036,640 | A | 3/2000 | Corace et al. |
| 6,036,685 | A | 3/2000 | Mueller |
| 6,053,927 | A | 4/2000 | Hamas |
| 6,053,937 | A | 4/2000 | Edwards et al. |
| 6,066,160 | A | 5/2000 | Colvin et al. |
| 6,068,603 | A | 5/2000 | Suzuki |
| 6,068,629 | A | 5/2000 | Haissaguerre et al. |
| 6,071,233 | A | 6/2000 | Ishikawa et al. |
| 6,074,408 | A | 6/2000 | Freeman |
| 6,086,530 | A | 7/2000 | Mack |
| 6,090,105 | A | 7/2000 | Zepeda et al. |
| 6,090,108 | A | 7/2000 | McBrayer et al. |
| 6,090,129 | A | 7/2000 | Ouchi |
| 6,096,046 | A | 8/2000 | Weiss |
| 6,102,909 | A | 8/2000 | Chen et al. |
| 6,102,926 | A | 8/2000 | Tartaglia et al. |
| 6,106,473 | A | 8/2000 | Violante et al. |
| 6,106,521 | A | 8/2000 | Blewett et al. |
| 6,109,852 | A | 8/2000 | Shahinpoor et al. |
| 6,110,154 | A | 8/2000 | Shimomura et al. |
| 6,110,183 | A | 8/2000 | Cope |
| 6,113,593 | A | 9/2000 | Tu et al. |
| 6,117,144 | A | 9/2000 | Nobles et al. |
| 6,117,158 | A | 9/2000 | Measamer et al. |
| 6,139,555 | A | 10/2000 | Hart et al. |

(56) References Cited

U.S. PATENT DOCUMENTS

| | | | |
|---|---|---|---|
| 6,141,037 A | 10/2000 | Upton et al. | |
| 6,146,391 A | 11/2000 | Cigaina | |
| 6,148,222 A | 11/2000 | Ramsey, III | |
| 6,149,653 A | 11/2000 | Deslauriers | |
| 6,149,662 A | 11/2000 | Pugliesi et al. | |
| 6,152,920 A | 11/2000 | Thompson et al. | |
| 6,156,006 A | 12/2000 | Brosens et al. | |
| 6,159,200 A | 12/2000 | Verdura et al. | |
| 6,165,175 A | 12/2000 | Wampler et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,169,269 B1 | 1/2001 | Maynard | |
| 6,170,130 B1 | 1/2001 | Hamilton et al. | |
| 6,179,776 B1 | 1/2001 | Adams et al. | |
| 6,179,832 B1 | 1/2001 | Jones et al. | |
| 6,179,837 B1 | 1/2001 | Hooven | |
| 6,183,420 B1 | 2/2001 | Douk et al. | |
| 6,190,353 B1 | 2/2001 | Makower et al. | |
| 6,190,383 B1 | 2/2001 | Schmaltz et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,206,904 B1 | 3/2001 | Ouchi | |
| 6,210,409 B1 | 4/2001 | Ellman et al. | |
| 6,214,007 B1 | 4/2001 | Anderson | |
| 6,214,028 B1 | 4/2001 | Yoon et al. | |
| 6,216,043 B1 | 4/2001 | Swanson et al. | |
| 6,228,096 B1 | 5/2001 | Marchand | |
| 6,231,506 B1 | 5/2001 | Hu et al. | |
| 6,234,958 B1 | 5/2001 | Snoke et al. | |
| 6,245,079 B1 | 6/2001 | Nobles et al. | |
| 6,246,914 B1 | 6/2001 | de la Rama et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,314,963 B1 | 11/2001 | Vaska et al. | |
| 6,322,578 B1 | 11/2001 | Houle et al. | |
| 6,325,534 B1 | 12/2001 | Hawley et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,350,278 B1 | 2/2002 | Lenker et al. | |
| 6,352,503 B1 | 3/2002 | Matsui et al. | |
| 6,352,543 B1 | 3/2002 | Cole | |
| 6,355,013 B1 | 3/2002 | van Muiden | |
| 6,355,035 B1 | 3/2002 | Manushakian | |
| 6,361,534 B1 | 3/2002 | Chen et al. | |
| 6,364,879 B1 | 4/2002 | Chen et al. | |
| 6,368,340 B2 | 4/2002 | Malecki et al. | |
| 6,371,956 B1 | 4/2002 | Wilson et al. | |
| 6,379,366 B1 | 4/2002 | Fleischman et al. | |
| 6,383,195 B1 | 5/2002 | Richard | |
| 6,383,197 B1 | 5/2002 | Conlon et al. | |
| 6,387,671 B1 | 5/2002 | Rubinsky et al. | |
| 6,391,029 B1 | 5/2002 | Hooven et al. | |
| 6,398,708 B1 | 6/2002 | Hastings et al. | |
| 6,402,735 B1 | 6/2002 | Langevin | |
| 6,402,746 B1 | 6/2002 | Whayne et al. | |
| 6,406,440 B1 | 6/2002 | Stefanchik | |
| 6,409,727 B1 | 6/2002 | Bales et al. | |
| 6,409,733 B1 | 6/2002 | Conlon et al. | |
| 6,419,639 B2 | 7/2002 | Walther et al. | |
| 6,419,641 B1 | 7/2002 | Mark et al. | |
| 6,427,089 B1 | 7/2002 | Knowlton | |
| 6,431,500 B1 | 8/2002 | Jacobs et al. | |
| 6,436,107 B1 | 8/2002 | Wang et al. | |
| 6,443,970 B1 * | 9/2002 | Schulze et al. | 606/171 |
| 6,443,988 B2 | 9/2002 | Felt et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,458,076 B1 | 10/2002 | Pruitt | |
| 6,464,701 B1 | 10/2002 | Hooven et al. | |
| 6,464,702 B2 * | 10/2002 | Schulze et al. | 606/51 |
| 6,470,218 B1 | 10/2002 | Behl | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,627 B1 | 12/2002 | Komi | |
| 6,491,691 B1 | 12/2002 | Morley et al. | |
| 6,493,590 B1 | 12/2002 | Wessman et al. | |
| 6,494,893 B2 | 12/2002 | Dubrul et al. | |
| 6,500,176 B1 * | 12/2002 | Truckai et al. | 606/51 |
| 6,503,192 B1 | 1/2003 | Ouchi | |
| 6,506,190 B1 | 1/2003 | Walshe | |
| 6,508,827 B1 | 1/2003 | Manhes | |
| 6,514,239 B2 | 2/2003 | Shimmura et al. | |
| 6,520,954 B2 | 2/2003 | Ouchi | |
| 6,526,320 B2 | 2/2003 | Mitchell | |
| 6,527,782 B2 | 3/2003 | Hogg et al. | |
| 6,530,922 B2 | 3/2003 | Cosman et al. | |
| 6,535,764 B2 | 3/2003 | Imran et al. | |
| 6,537,200 B2 | 3/2003 | Leysieffer et al. | |
| 6,543,456 B1 | 4/2003 | Freeman | |
| 6,551,270 B1 | 4/2003 | Bimbo et al. | |
| 6,554,766 B2 | 4/2003 | Maeda et al. | |
| 6,554,823 B2 | 4/2003 | Palmer et al. | |
| 6,554,829 B2 | 4/2003 | Schulze et al. | |
| 6,558,384 B2 | 5/2003 | Mayenberger | |
| 6,562,034 B2 | 5/2003 | Edwards et al. | |
| 6,562,035 B1 | 5/2003 | Levin | |
| 6,562,052 B2 | 5/2003 | Nobles et al. | |
| 6,569,159 B1 | 5/2003 | Edwards et al. | |
| 6,572,629 B2 | 6/2003 | Kalloo et al. | |
| 6,572,635 B1 | 6/2003 | Bonutti | |
| 6,575,988 B2 | 6/2003 | Rousseau | |
| 6,579,311 B1 | 6/2003 | Makower | |
| 6,581,889 B2 | 6/2003 | Carpenter et al. | |
| 6,585,642 B2 | 7/2003 | Christopher | |
| 6,585,717 B1 | 7/2003 | Wittenberger et al. | |
| 6,587,750 B2 | 7/2003 | Gerbi et al. | |
| 6,592,559 B1 | 7/2003 | Pakter et al. | |
| 6,592,603 B2 | 7/2003 | Lasner | |
| 6,602,262 B2 | 8/2003 | Griego et al. | |
| 6,605,105 B1 | 8/2003 | Cuschieri et al. | |
| 6,610,072 B1 | 8/2003 | Christy et al. | |
| 6,610,074 B2 | 8/2003 | Santilli | |
| 6,613,038 B2 | 9/2003 | Bonutti et al. | |
| 6,613,068 B2 | 9/2003 | Ouchi | |
| 6,616,632 B2 | 9/2003 | Sharp et al. | |
| 6,620,193 B1 | 9/2003 | Lau et al. | |
| 6,623,448 B2 | 9/2003 | Slater | |
| 6,626,919 B1 | 9/2003 | Swanstrom | |
| 6,632,229 B1 | 10/2003 | Yamanouchi | |
| 6,632,234 B1 | 10/2003 | Kieturakis et al. | |
| 6,638,275 B1 | 10/2003 | McGaffigan et al. | |
| 6,638,286 B1 | 10/2003 | Burbank et al. | |
| 6,645,225 B1 | 11/2003 | Atkinson | |
| 6,652,518 B2 | 11/2003 | Wellman et al. | |
| 6,652,521 B2 | 11/2003 | Schulze | |
| 6,652,551 B1 | 11/2003 | Heiss | |
| 6,656,194 B1 | 12/2003 | Gannoe et al. | |
| 6,663,641 B1 | 12/2003 | Kovac et al. | |
| 6,663,655 B2 | 12/2003 | Ginn et al. | |
| 6,666,854 B1 | 12/2003 | Lange | |
| 6,672,338 B1 | 1/2004 | Esashi et al. | |
| 6,673,058 B2 | 1/2004 | Snow | |
| 6,673,087 B1 | 1/2004 | Chang et al. | |
| 6,673,092 B1 | 1/2004 | Bacher | |
| 6,679,882 B1 * | 1/2004 | Kornerup | 606/51 |
| 6,685,628 B2 | 2/2004 | Vu | |
| 6,685,724 B1 | 2/2004 | Haluck | |

(56) References Cited

U.S. PATENT DOCUMENTS

| | | |
|---|---|---|
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 * | 9/2006 | Dycus et al. .................. 606/49 |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |

(56) References Cited

U.S. PATENT DOCUMENTS

| | | |
|---|---|---|
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 * | 12/2006 | Sremcich et al. ............... 29/854 |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,222 B2 | 7/2008 | Asakura |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 * | 6/2009 | Schechter et al. ............... 606/50 |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 * | 6/2010 | Couture ........................ 606/171 |
| 7,749,161 B2 | 7/2010 | Beckman et al. |
| 7,753,933 B2 | 7/2010 | Ginn et al. |
| 7,758,577 B2 * | 7/2010 | Nobis et al. ..................... 606/45 |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,771,416 B2 | 8/2010 | Spivey et al. |
| 7,771,437 B2 | 8/2010 | Hogg et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,828,186 B2 | 11/2010 | Wales |
| 7,833,156 B2 | 11/2010 | Williams et al. |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,892,220 B2 | 2/2011 | Faller et al. |

(56) References Cited

U.S. PATENT DOCUMENTS

| | | |
|---|---|---|
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,034,046 B2 | 10/2011 | Eidenschink |
| 8,048,067 B2 | 11/2011 | Davalos et al. |
| 8,057,510 B2 | 11/2011 | Ginn et al. |
| 8,062,311 B2 | 11/2011 | Litscher et al. |
| 8,066,632 B2 | 11/2011 | Dario et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,118,821 B2 | 2/2012 | Mouw |
| 8,147,424 B2 | 4/2012 | Kassab et al. |
| 8,157,813 B2 | 4/2012 | Ko et al. |
| 8,182,414 B2 | 5/2012 | Handa et al. |
| 8,206,295 B2 | 6/2012 | Kaul |
| 8,221,310 B2 | 7/2012 | Saadat et al. |
| 8,303,581 B2 | 11/2012 | Arts et al. |
| 8,430,811 B2 | 4/2013 | Hess et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191464 A1* | 10/2003 | Kidooka .......... 606/45 |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |

(56) References Cited

U.S. PATENT DOCUMENTS

| | | |
|---|---|---|
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1* | 11/2005 | Nobis et al. .................. 606/45 |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0189980 A1* | 8/2006 | Johnson et al. .................. 606/51 |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016255 A1 | 1/2007 | Korb |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |

(56) References Cited

U.S. PATENT DOCUMENTS

| | | |
|---|---|---|
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |

(56) References Cited

U.S. PATENT DOCUMENTS

| | | |
|---|---|---|
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227828 A1 | 9/2009 | Swain et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0076460 A1 | 3/2010 | Taylor et al. |
| 2010/0081877 A1 | 4/2010 | Vakharia |
| 2010/0087813 A1 | 4/2010 | Long |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0217367 A1 | 8/2010 | Belson |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0029335 A1 | 2/2012 | Sudam et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |
| 2012/0238796 A1 | 9/2012 | Conlon |
| 2012/0330306 A1 | 12/2012 | Long et al. |
| 2013/0090666 A1 | 4/2013 | Hess et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |

(56) References Cited

FOREIGN PATENT DOCUMENTS

| | | |
|---|---|---|
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| JP | 2006-343510 A | 12/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

K. Sumiyama et al., "Endoscopic Caps," Tech. Gastrointest. Endosc., vol. 8, pp. 28-32, 2006.

F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

Endoscopic Retrograde Cholangiopancreatogram (ERCP); [online] URL:http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

(56) References Cited

OTHER PUBLICATIONS

D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.inj.com/connect/news/product/20090603_120000; accessed Aug. 28, 2009 (3 pages).
Castellvi et al., "Hybrid Transvaginal NOTES Sleeve Gastrectomy in a Porcine Model Using A Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using A Magnetically Anchored Camera and Novel Instrumentation," Poster submitted along with Abstract at SAGES Annual Meeting in Phoenix, AZ, Apr. 22, 2009 (1 page).
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 11/986,420, filed Nov. 27, 2007.
U.S. Appl. No. 11/897,676, filed Aug. 31, 2007.
Michael S. Kavic, M.D., "Natural Orifice Translumenal Endoscopic Surgery: "NOTES"", JSLS, vol. 10, pp. 133-134 (2006).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
"Z-Offset Technique Used in the Introduction of Trocar During Laparoscopic Surgery," M.S. Hershey NOTES Presentation to EES NOTES Development Team, Sep. 27, 2007.
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

(56) References Cited

OTHER PUBLICATIONS

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
U.S. Appl. No. 11/706,460, filed Feb. 15, 2007.
U.S. Appl. No. 11/706,591, filed Feb. 15, 2007.
U.S. Appl. No. 11/706,685, filed Feb. 15, 2007.
U.S. Appl. No. 11/706,766, filed Feb. 15, 2007.
U.S. Appl. No. 11/706,811, filed Feb. 15, 2007.
U.S. Appl. No. 11/707,831, filed Feb. 16, 2007.
U.S. Appl. No. 11/715,710, filed Mar. 8, 2007.
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
Written Opinion for PCT/US2008/084311, Jul. 10, 2009 (9 pages).
International Preliminary Report on Patentability for PCT/US2008/084311, May 10, 2010 (9 pages).
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
Ethicon, Inc., "Wound Closure Manual: Chapter 3 (The Surgical Needle)," 15 pages, (1994).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818 filed Mar. 15, 2012.
U.S. Appl. No. 13/425,103, filed Mar. 20, 2012.
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).

\* cited by examiner

BIPOLAR FORCEPS

RELATED APPLICATION

The present application is related to U.S. patent application Ser. No. 11/986,420, entitled BIPOLAR FORCEPS, now U.S. Pat. No. 8,262,655, which is a commonly-owned U.S. patent application filed concurrently herewith, the entire disclosure of which is hereby incorporated by reference herein.

BACKGROUND

1. Field of the Invention

The present invention generally relates to electrical ablation surgical instruments and, more particularly, to bipolar forceps for performing various surgical techniques.

2. Description of the Related Art

Previous bipolar forceps have included a grasping device which is configured to grasp and manipulate soft tissue, for example. In various circumstances, the grasping device has included a first electrode and a second electrode where, when one of the electrodes is brought into close opposition to the other electrode, an electrical current can pass therebetween. More particularly, when soft tissue is captured between the electrodes, current can be supplied to the first electrode and flow to the second electrode through the soft tissue. In such circumstances, the current can cauterize, vaporize, and/or otherwise treat, the soft tissue. Previous bipolar forceps, referring to U.S. Pat. No. 5,944,718, the entire disclosure of which is hereby incorporated be reference herein, have included a first electrode which can be pivoted relative to a stationary second electrode. These forceps have further included a first wire attached to the first electrode where the first wire is configured to supply current to the first electrode from an electrical source. In addition, these forceps have included a second wire which is attached to the second electrode where the second wire is configured to complete the electrical circuit and return the current back to the electrical source. In order for the first wire to remain in electrical communication with the first electrode when the first, or movable, jaw member is pivoted, the first wire must often bend and/or stretch in order to accommodate this movement. In some circumstances, such bending or stretching may cause the wire to break and/or the insulation covering the wire to become chaffed, thereby rendering the surgical instrument inoperative or unreliable. What is needed is an improvement over the foregoing.

SUMMARY

In at least one form of the invention, a bipolar forceps can include a first electrode, a second electrode, and a conductor, or wire, operably connected to an electrical source, for example, wherein the conductor can be selectively placed in electrical communication with the first electrode when the first electrode is moved between open and closed positions. In various embodiments, the wire can include a contact end which is not in contact with the first electrode when the first electrode is in its open position. In such an open position, the first electrode may not be in electrical communication with the electrical source and, as a result, current may not flow through the first electrode. In at least one such embodiment, the first electrode can be moved into its closed position such that the first electrode is in contact with the contact end of the wire. In such a closed position, the first electrode may be in electrical communication with the electrical source allowing current to flow through the first electrode. As a result of the above, the first electrode can move relative to the wire such that the wire does not have to move with the first electrode when the first electrode is moved between its open and closed positions and, as a result, the likelihood that the wire may become damaged or broken can be reduced.

In at least one form of the invention, a bipolar forceps can include two or more electrodes wherein the electrodes can be positioned against, or adjacent to, a vessel, such as a blood vessel, for example, and energy can be supplied to the electrodes. In various circumstances, the energy can be sufficient to at least substantially seal the vessel such that blood does not substantially flow therethrough. In at least one surgical technique, the bipolar forceps can be used to seal the vessel in two locations such that the vessel can be incised, or transected, at a location positioned intermediate the two seal locations. In at least one embodiment, the bipolar forceps can include a cutting element which can be configured to incise the vessel. In various embodiments, the cutting element can include a sharp edge which can be moved relative to the vessel. In at least one embodiment, the cutting element can be electrically connected to a source of energy wherein the energized cutting element can be configured to incise the tissue.

In at least one form of the invention, a bipolar forceps can include first and second electrodes positioned within first and second jaw members, respectively, wherein at least one of the jaw members can include a substantially tapered profile. In various surgical techniques, the jaw members can be positioned in a substantially closed position such that the distal end of the jaw members can be positioned intermediate a vessel, for example, and tissue at least partially surrounding the vessel. Thereafter, in at least one surgical technique, the jaw members can be opened in order to pull the vessel away from the soft tissue. In various techniques, the jaw members can be opened and closed repeatedly to enlarge a hole between the vessel and the tissue and/or otherwise separate the vessel from the tissue. In at least one embodiment, at least one of the jaw members can include ridges, teeth, and/or a textured outer surface configured to grip the soft tissue and/or vessel.

BRIEF DESCRIPTION OF THE DRAWINGS

The above-mentioned and other features and advantages of the various embodiments of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 1:
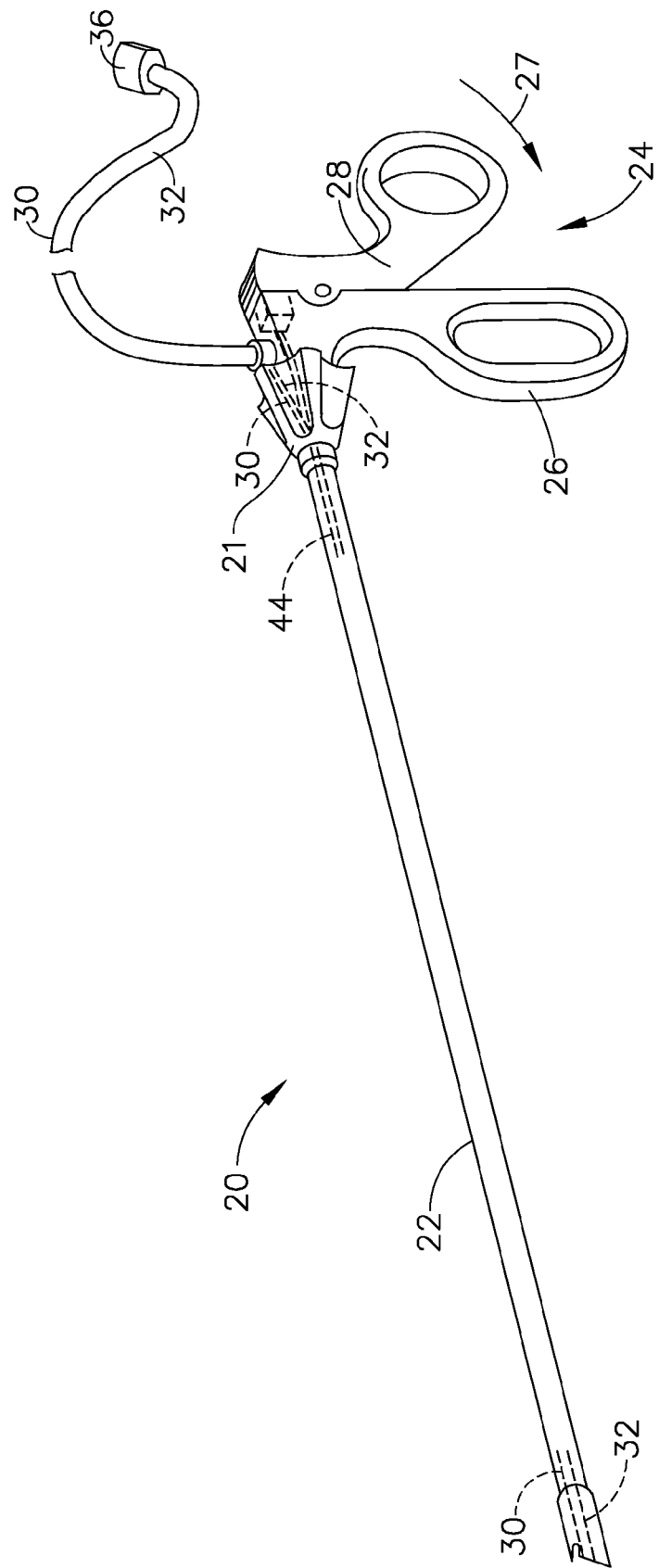
FIG. 1 is a perspective view of a hand piece and a shaft assembly of a surgical instrument in accordance with an embodiment of the present invention.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The various embodiments described herein are related to electrical therapy ablation devices. Generally, electrical therapy ablation devices can comprise electrodes that can be positioned in, or in proximity to, a tissue treatment region, or target site, within a patient. These devices, and the surgical techniques for using the same, may be employed to treat tissue masses, tissue tumors, and lesions, for example, (all of which are hereinafter referred to as 'diseased tissue') at the tissue treatment region. In various embodiments, these devices can be utilized in open surgical procedures as well as external and non-invasive medical procedures. In other various embodiments, these devices may be adapted to provide minimally invasive access to the tissue treatment region or anatomic location, such as lung and liver tissue, for example, in order to diagnose and treat the condition at the tissue treatment region more accurately and effectively. In various embodiments, portions of the electrical therapy ablation devices may be introduced in the tissue treatment region endoscopically (e.g., laparoscopically and/or thoracoscopically), or through a trocar extending through a small incision. Portions of other devices may be introduced into the tissue treatment region by way of a natural orifice through a cannula or catheter. Minimally invasive procedures which introduce medical instruments to a tissue treatment region through a natural opening of the patient are known as Natural Orifice Translumenal Endoscopic Surgery (NOTES)™. In other embodiments, portions of the electrical therapy devices can be introduced percutaneously or in any combination of the methods described above.

Once positioned, the electrical therapy electrodes can deliver electrical current to the treatment region. The electrical current can be generated by a control unit or generator located external to the patient, for example, where the electrical current may be characterized by a particular waveform in terms of frequency, amplitude, and pulse width. Depending on the diagnostic or therapeutic treatment rendered, the diseased tissue can be electrically ablated or destroyed. More particularly, the electrical therapy ablation devices may be employed to deliver sufficient energy to the diseased tissue to ablate or destroy tumors, masses, lesions, and other abnormal tissue growths. In at least one embodiment, the electrical therapy ablation devices and techniques described herein may be employed in the treatment of cancer by quickly creating necrosis and destroying live cancerous tissue in-vivo. Such devices and techniques are further described in a commonly-owned, co-pending U.S. patent application Ser. No. 11/897,676, entitled ELECTRICAL ABLATION SURGICAL INSTRUMENTS, filed on Aug. 31, 2007, the entire disclosure of which is hereby incorporated by reference herein.

In various embodiments, electrical therapy ablation may employ electroporation, or electropermeabilization, techniques where an externally applied electric field (electric potential) significantly increases the electrical conductivity and permeability of a cell plasma membrane. Electroporation is the generation of a destabilizing electric potential across such biological membranes. In electroporation, pores are formed when the voltage across the cell plasma membrane exceeds its dielectric strength. Electroporation destabilizing electric potentials are generally in the range of several hundred volts across a distance of several millimeters. Below certain magnitude thresholds, the electric potentials may be applied across a biological membrane as a way of introducing some substance into a cell, such as loading it with a molecular probe, a drug that can change the function of the cell, a piece of coding DNA, or increasing the uptake of drugs in cells. If the strength of the applied electrical field and/or duration of exposure to it are suitably chosen, the pores formed by the electrical pulse reseal after a short period of time, during such period extra-cellular compounds may enter into the cell. Below a certain field threshold, the process is reversible and the potential does not permanently damage the cell membrane. This process may be referred to as reversible electroporation (RE). On the other hand, excessive exposure of live cells to large electric fields can cause apoptosis and/or necrosis—the processes that result in cell death. Excessive exposure of live cells to large excessive electrical fields or potentials across the cell membranes causes the cells to die and therefore may be referred to as irreversible electroporation (IRE). Electroporation may be performed with devices called electroporators. These appliances can create the electric current and send it through the cell. Electroporators may comprise two or more metallic (e.g., aluminum) electrically conductive electrodes connected to an energy source. The energy source can generate an electric field having a suitable characteristic waveform output in terms of frequency, amplitude, and pulse width.

In various embodiments, an electrical ablation system may be employed in conjunction with a flexible endoscope, such as a GIF-100 model available from Olympus Corporation, for example. In at least one such embodiment, the endoscope, a laparoscope, or a thoracoscope, for example, may be introduced into the patient trans-anally through the colon, the abdomen via an incision or keyhole and a trocar, or trans-orally through the esophagus, for example. These devices can assist the surgeon to guide and position the electrical ablation system near the tissue treatment region to treat diseased tissue on organs such as the liver, for example. In another embodiment, these devices may be positioned to treat diseased tissue near the gastrointestinal (GI) tract, esophagus, and/or lung, for example. In various embodiments, the endoscope may comprise a flexible shaft where the distal end of flexible shaft may comprise a light source, a viewing port, and at least one working channel. In at least one such embodiment, the viewing port can transmit an image within its field of view to an optical device such as a charge coupled device (CCD) camera within the endoscope, for example, so that an operator may view the image on a display monitor (not shown).

In various embodiments, referring to FIG. 1, surgical instrument, or bipolar forceps, 20 can include an end effector, shaft assembly 22, and hand piece 24. In at least one embodiment, shaft assembly 22 can comprise a flexible shaft of an endoscopic surgical instrument wherein at least portions of the end effector and shaft assembly 22 can be configured to be positioned within and/or inserted through a working channel of an endoscope. Hand piece 24 can be configured to be grasped by a surgeon and, in at least one embodiment, hand piece 24 can comprise a pistol grip including stationary member 26 and movable member, or trigger, 28. In use, as described in greater detail below, trigger 28 can be moved toward stationary member 26 as indicated by arrow 27, for example, in order to operate the end effector within a surgical site. Although not illustrated, surgical instrument 20 can include a switch which can place the end effector in electrical communication with an electrical source, or generator, via wires 30 and 32. In at least one embodiment, wires 30 and 32 can terminate in connector 34 where, referring to FIG. 2, connector 34 can be configured to be operably connected to connector 36 of generator 38.

In various embodiments, referring to FIGS. 3-9, an end effector, such as end effector 50, for example, can include a grasping device comprising first jaw member 52 and second jaw member 54, where at least one of jaw members 52 and 54 can be moved relative to the other. In at least one embodiment, jaw members 52 and 54 can be movably coupled to housing, or clevis, 56 such that they can be moved, or pivoted, between open and closed positions about pivot pin 58. In use, jaw members 52 and 54 can be positioned in their closed, or at least partially closed, positions before they are inserted into a surgical site through a trocar, for example. In various embodiments, jaw members 52 and 54 can be configured such that they can be positioned within and/or inserted through a working channel of an endoscope. Once positioned within the surgical site, jaw members 52 and 54 can then be reopened. In their open position, jaw members 52 and 54 can be positioned on, or relative to, the targeted soft tissue within the surgical site. Thereafter, in at least one embodiment, jaw members 52 and 54 can be pivoted into their closed position to hold the soft tissue therebetween. In various embodiments, at least one of jaw members 52 and 54 can include serrations, or teeth, 60 which can be configured to securely hold the soft tissue therebetween.

In order to more easily position end effector 50, the shaft assembly extending between end effector 50 and hand piece 24 can be flexible. In at least one embodiment, referring to FIG. 3, shaft assembly 80 can include a flexible elongate member 82 and a flexible coil spring 84 positioned therearound. In various embodiments, referring to FIGS. 7-11, a surgical instrument can further include adapter assembly 86 for operably connecting end effector 50 to shaft assembly 80. In at least one embodiment, adapter assembly 86 can include ring capture 88 which can include an aperture therein, or any other suitable feature, for receiving and retaining an end of coil spring 84. Adapter assembly 86 can further include bushing coupler 83 which can include projection 85, or any other suitable feature, which can be fixedly connected to housing 56. In addition to the above, adapter assembly 86 can also include inner housing coupler 87 which can be configured to connect ring capture 88 to bushing coupler 83 such that end effector 50 is correspondingly coupled to shaft assembly 80.

In order to move jaw members 52 and 54 between their open and closed positions as described above, trigger 28 of hand piece 24 can be pivoted relative to stationary member 26 such that trigger 28 can displace actuator, or rod, 44 (FIG. 1) relative to shaft 22. In various embodiments, actuator 44 can be round, or any other suitable shape, and can be either solid or tubular. In either event, referring to FIG. 6, actuator rod 44 can be operably engaged with actuator 46 such that, when trigger 28 is pivoted toward stationary member 26 as described above, actuator rod 44 and actuator 46 can be slid proximally such that actuator 46 pulls on jaw links 53 and 55. It will be appreciated that the terms "proximal" and "distal" are used herein with reference to a clinician gripping hand piece 24 of instrument 20, for example. Thus, end effector 50 is distal with respect to hand piece 24. When jaw links 53 and 55 are pulled proximally, jaw links 53 and 55 can apply a force to jaws 52 and 54, respectively, such that they are pivoted about pivot pin 58 into their closed positions. In order to move jaws 52 and 54 into their open positions, trigger 28 can be moved away from stationary portion 26 and, correspondingly, actuator rod 44 and actuator 46 can be moved distally by trigger 28. Similarly, actuator 46 can move links 53 and 55 distally such that such that links 53 and 55 apply a force to jaws 52 and 54 and rotate them about pivot pin 58 in the opposite, or open, direction. Now referring to another exemplary embodiment illustrated in FIGS. 13 and 14, when trigger 28' is pivotally moved (e.g., squeezed) in the direction indicated by arrow 29, actuator rod 44 can be moved in the direction indicated by arrow 47, and the first and second jaw members 52 and 54 can close in the direction indicated by arrow 49. When trigger 28' is pivotally moved (e.g., released) in the direction indicated by arrow 31, actuator 44 can be moved in the direction indicated by arrow 45, and the first and second jaw members can open in the direction indicated by arrow 51.

Further to the above, in various embodiments, at least a portion of the distal end of actuator rod 44 can be fixedly received in shaft collar 66' (FIG. 14) such that, when collar 66' is moved by trigger 28', actuator 44 can be moved proximally and distally as described above. In at least one embodiment, trigger 28' can be operably engaged with pin 67' in shaft collar 66' such that the rotational movement of trigger 28' can be converted to translational movement of shaft collar 66'. More particularly, although not illustrated, trigger 28' can include a cam slot which is configured to receive pin 67' such that, when trigger 28' is rotated as described above, the sidewalls of the slot can motivate shaft collar 66', and actuator 44 operably engaged therewith, along a path defined by housing portion 65'. In various embodiments, although not illustrated, hand piece 24' can further include a biasing member, or spring, which is configured to bias trigger 28', and jaw members 52 and 54, into one of a closed or open position.

Figure 14:
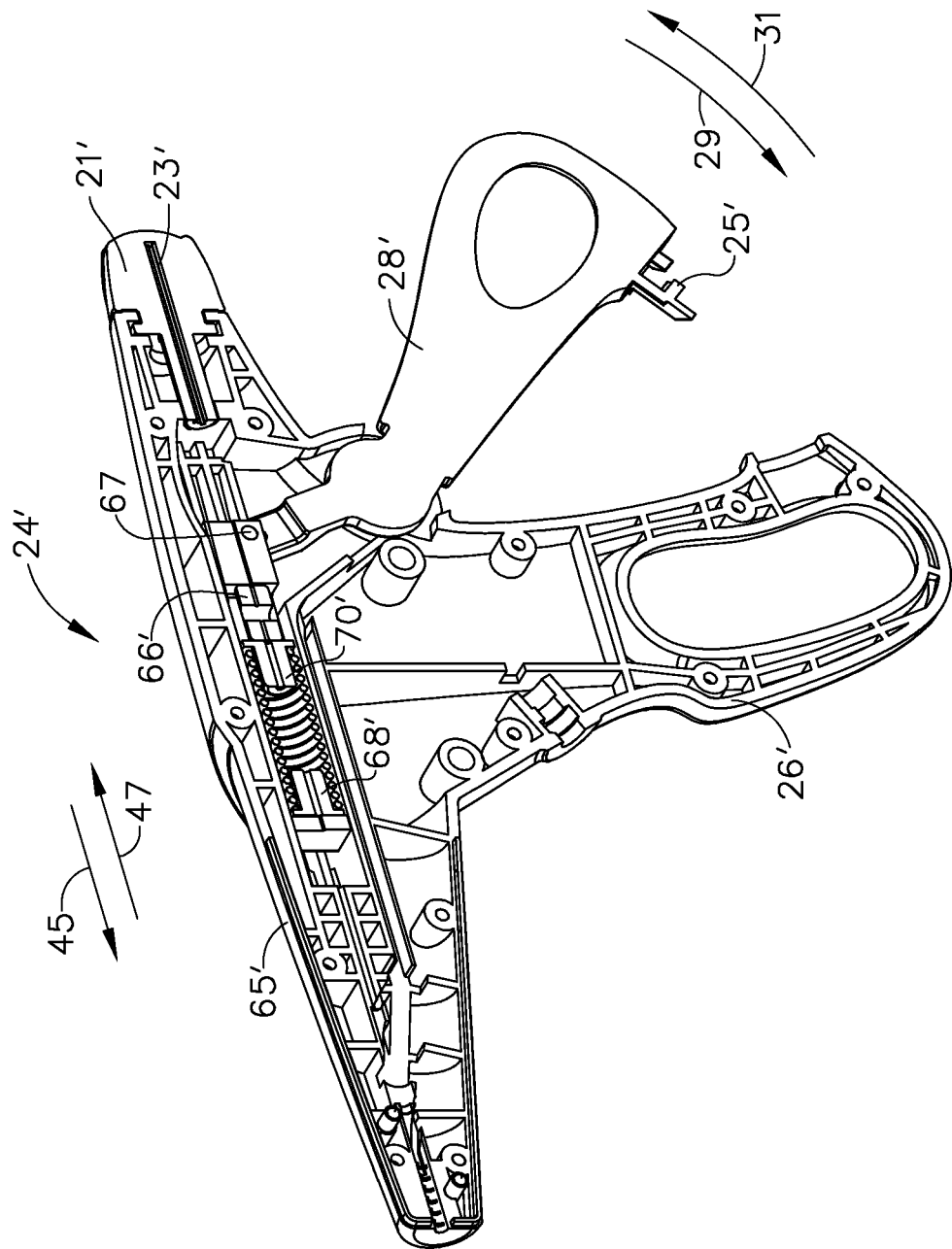
FIG. 14 is a cross-sectional view of a hand piece of the surgical instrument of FIG. 13.

In at least one embodiment, referring to FIG. 14, hand piece 24' can further include spring holders 68' and 70' where the spring can be positioned therebetween. In various embodiments, shaft collar 66' can be connected to one of spring holders 68' and 70' and the other of spring holders 68' and 70' can be connected to housing portion 65'. In such embodiments, when shaft collar 66' is moved relative to housing portion 65', one of spring holders 68' and 70' can be moved relative to the other such that the spring is placed in either tension or compression and can apply a spring force to trigger 28'. In at least one embodiment, when trigger 28' is released from its closed position as indicated by arrow 31, the spring force can bias trigger 28' into its open position as indicated by arrow 29. In various other embodiments, although not illustrated, trigger 28' can be biased into its closed position or any other suitable position. In at least one embodiment, trigger 28' can further include latch 25' which can be configured to hold trigger 28' to stationary portion 26' against the biasing force of the spring.

Figure 2:
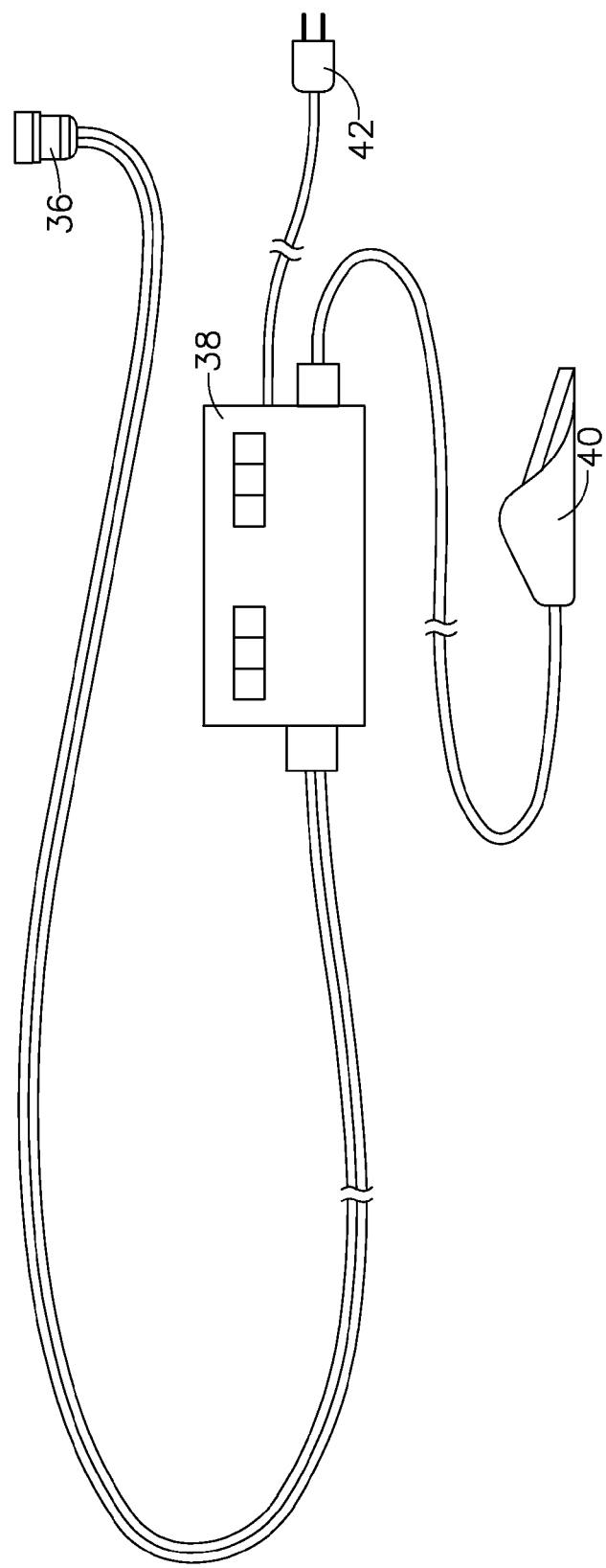
FIG. 2 is a schematic of an electrical source and an actuator for use with the surgical instrument of FIG. 1 in accordance with an embodiment of the present invention.
Figure 3:
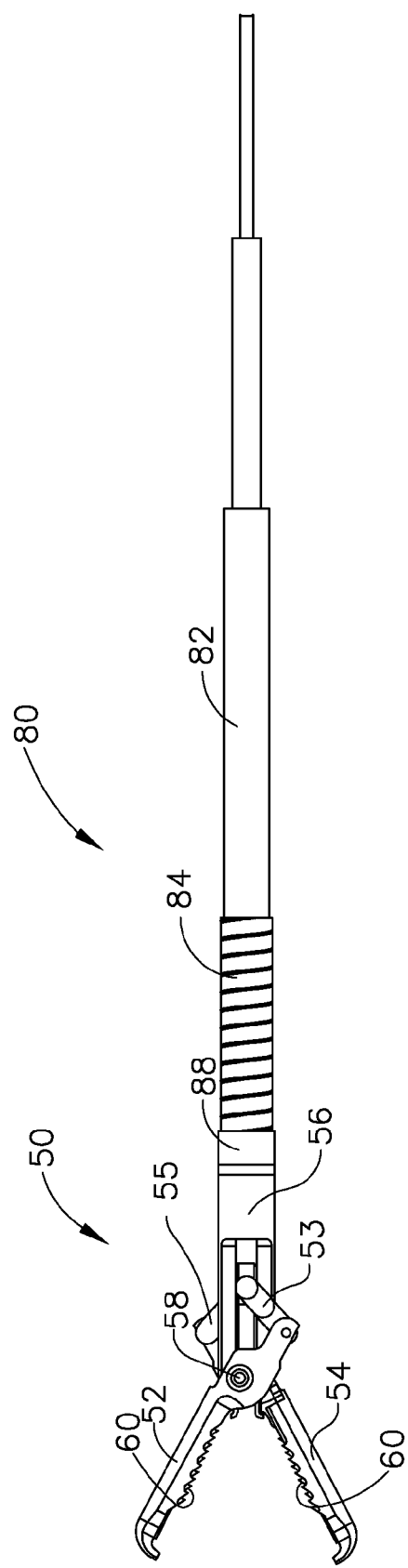
FIG. 3 is an elevational view of an end effector and a shaft assembly of a surgical instrument in accordance with an embodiment of the present invention.
Figure 13:
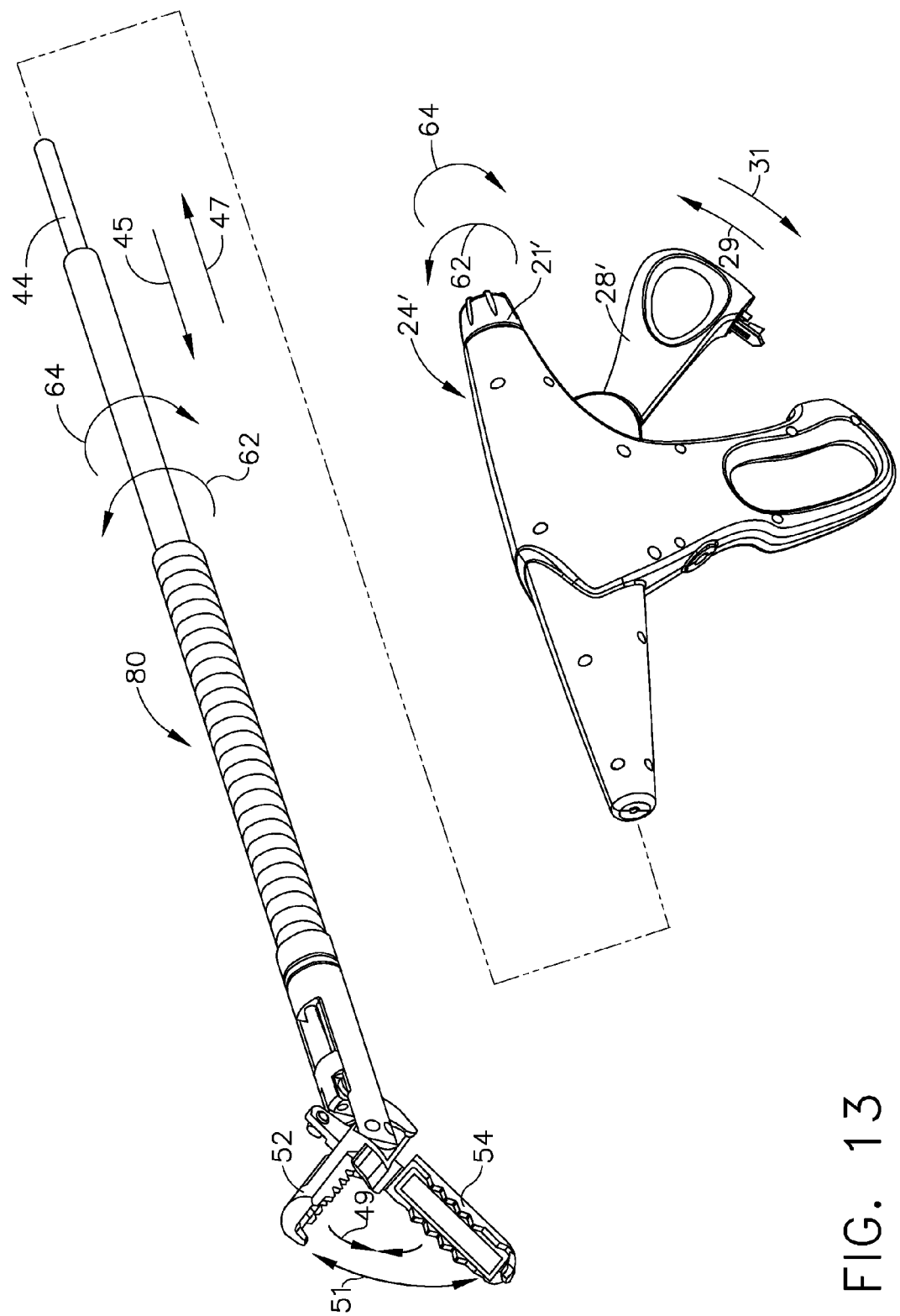
FIG. 13 is a perspective view of a surgical instrument in accordance with an embodiment of the present invention.

In various embodiments, referring to FIG. 2, hand piece 24 can include rotation knob 21 and, similarly, referring to FIG. 13, hand piece 24' can include rotation knob 21', where rotation knobs 21 and 21' can be configured to rotate an end effector of their respective surgical instruments relative to hand pieces 24 and 24'. In various embodiments, referring to FIGS. 13 and 14, a portion of actuator rod 44 can be slidably received within aperture 23' in rotation knob 21' wherein at least one of the actuator rod 44 and aperture 23' can include a non-circular profile. In such embodiments, the non-circular profile can allow actuator rod 44 to be rotated by knob 21' yet allow actuator rod 44 to slide relative thereto when it is moved proximally and distally by trigger 28' as described above. In at least one embodiment, when rotation knob 21' is rotated in the direction indicated by arrow 62, end effector 50 can also rotated in the direction indicated by arrow 62. Similarly, when rotation knob 21' is rotated in the direction indicated by arrow 64, end effector 50 can be rotated in the direction indicated by arrow 64. As a result of the above, jaw members 52 and 54 can be rotated within the surgical site and can be more accurately positioned by a surgeon.

Once end effector 50 has been positioned in a surgical site and jaw members 52 and 54 have been closed onto the soft tissue, as outlined above, the soft tissue can be treated by an electrical current that passes between jaw members 52 and 54. More particularly, in at least one embodiment, surgical instrument 20 can include an electrical circuit which is configured to receive an electrical current from current generator 38 (FIG. 2) and transmit the current to a first electrode 72 positioned within jaw member 52 via first conductor, or wire, 30. In various embodiments, the current can be conducted through the soft tissue positioned between jaw members 52 and 54 such that the current flows into a second electrode 74 positioned in second jaw member 54. The current can return to electrical generator 38 through second conductor, or wire, 32 to complete the circuit. In at least one such embodiment, generator 38 can include plug 42 which can be configured to provide commercially available current to generator 38 where generator 38 can be configured to transform the current as needed. In at least one embodiment, generator 38 can further include a switch, such as foot pedal 40, for example, which can be configured to place surgical instrument 20 in electrical communication with generator 38. In various embodiments, switch 40 can be utilized in addition to, or in lieu of, a switch on surgical instrument 20.

In various embodiments, a surgical instrument in accordance with the present invention can be configured such that at least one electrode can be selectively placed in electrical communication with a conductor associated therewith. In at least one embodiment, referring to FIGS. 5 and 6, first electrode 72 can be placed in electrical communication with first conductor 30 when jaw member 52 is in a first position and can be placed out of electrical communication with conductor 30 when jaw member 52 is in a second position, for example. In at least one such embodiment, first electrode 72 can be configured to abut, or contact, contact end 33 of conductor 30 when jaw 52 is in its closed, or at least a substantially closed, position such that current can flow between first electrode 72 and first conductor 30. In such embodiments, first electrode 72 can be moved away from contact end 33 when jaw member 52 is moved into its open, or at least a substantially open, position such that current cannot flow between first electrode 72 and first conductor 30. In various embodiments, conductor 30 does not have to be attached to first electrode 72 and, as a result, first electrode 72 can be moved relative to conductor 30.

Figure 5:
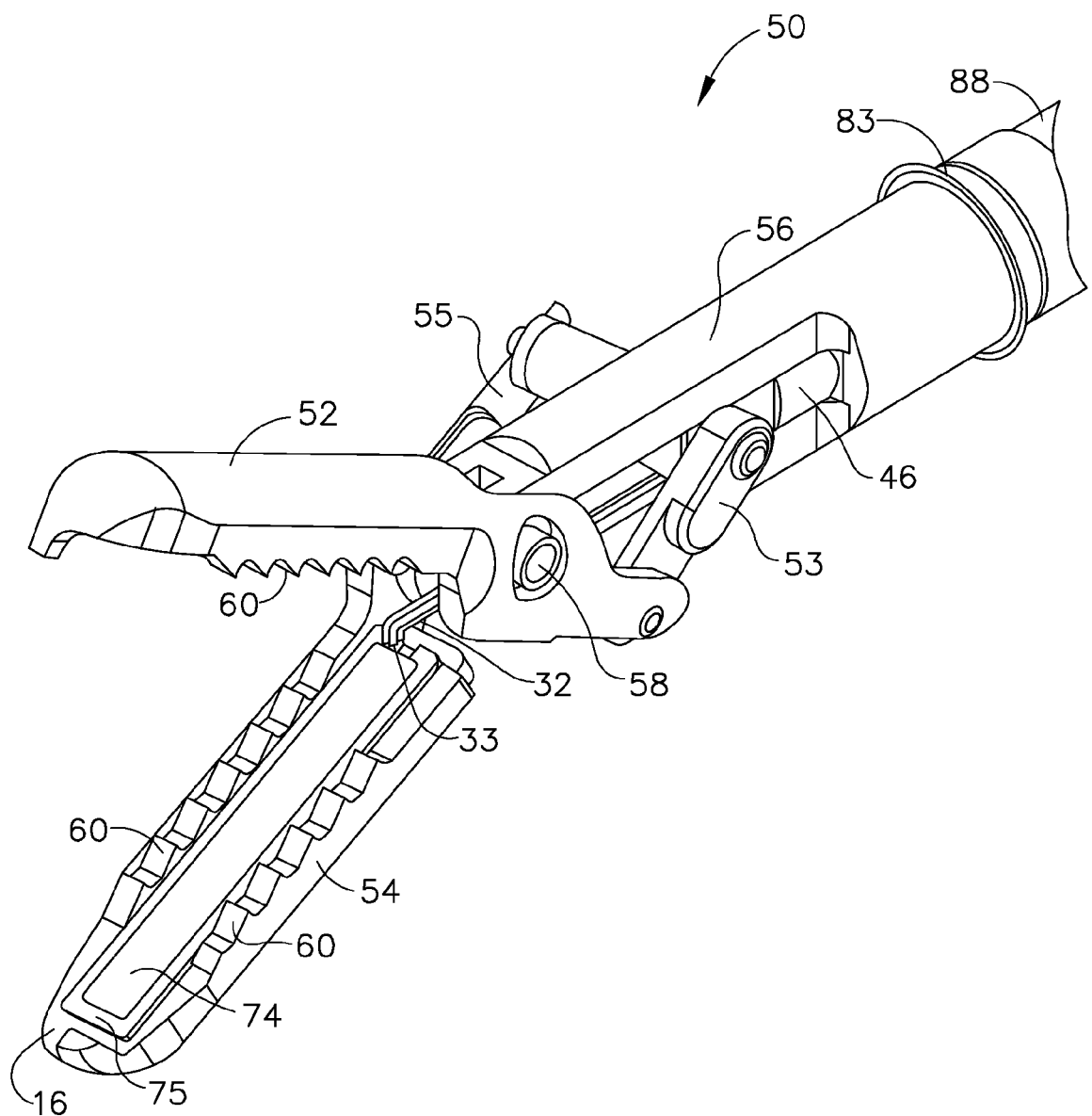
FIG. 5 is an additional perspective view of the end effector of FIG. 3.
Figure 6:
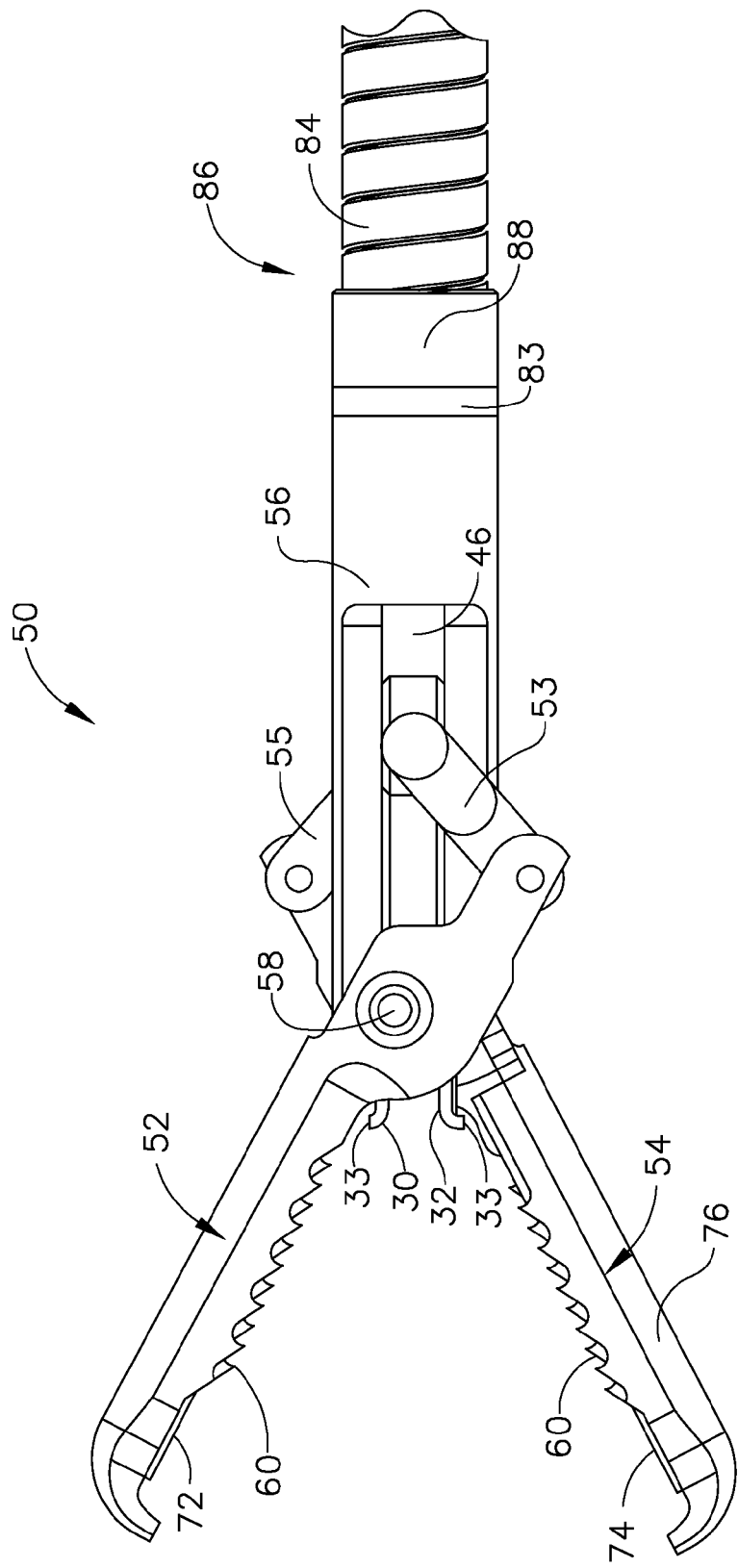
FIG. 6 is a left elevational view of the end effector of FIG. 3.
Figure 7:
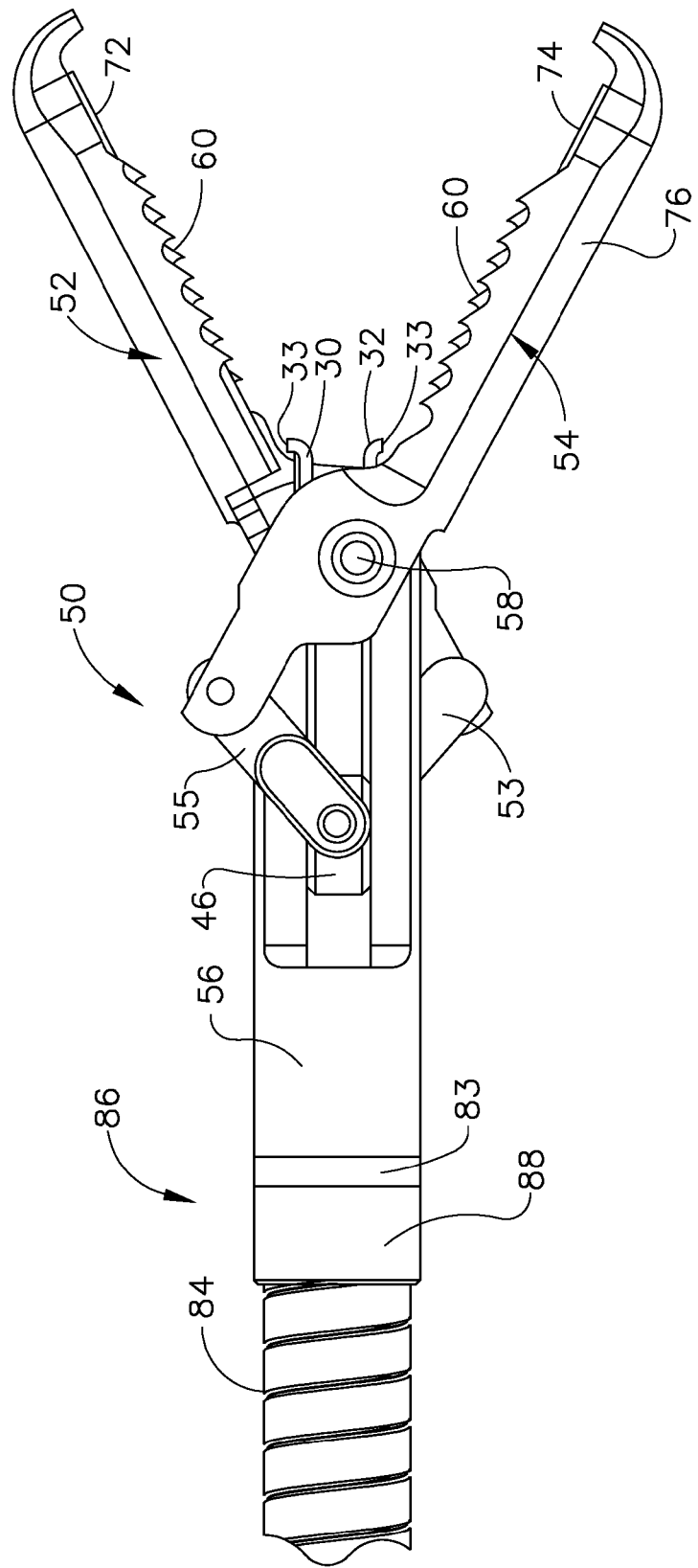
FIG. 7 is a right elevational view of the end effector of FIG. 3.
Figure 8:
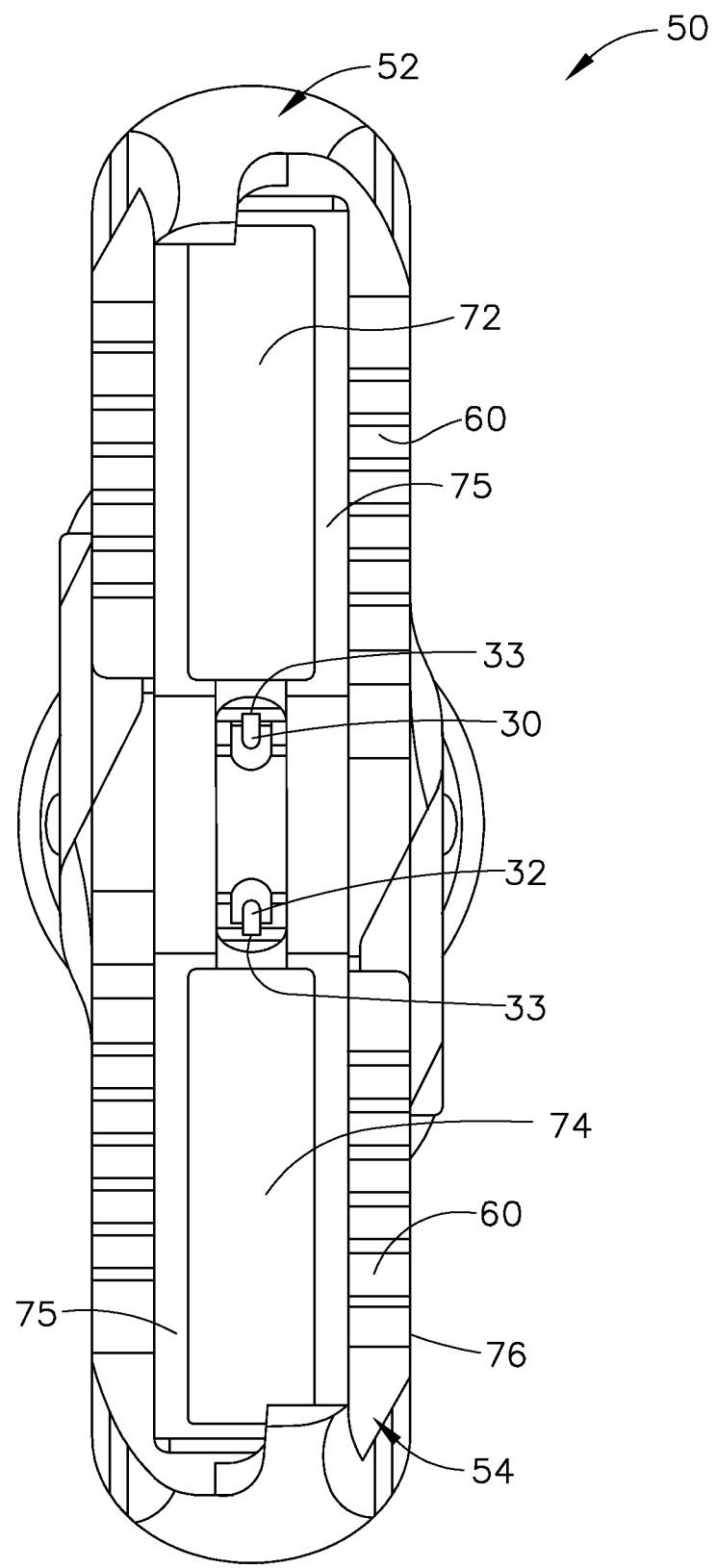
FIG. 8 is an end view of the end effector of FIG. 3
Figure 9:
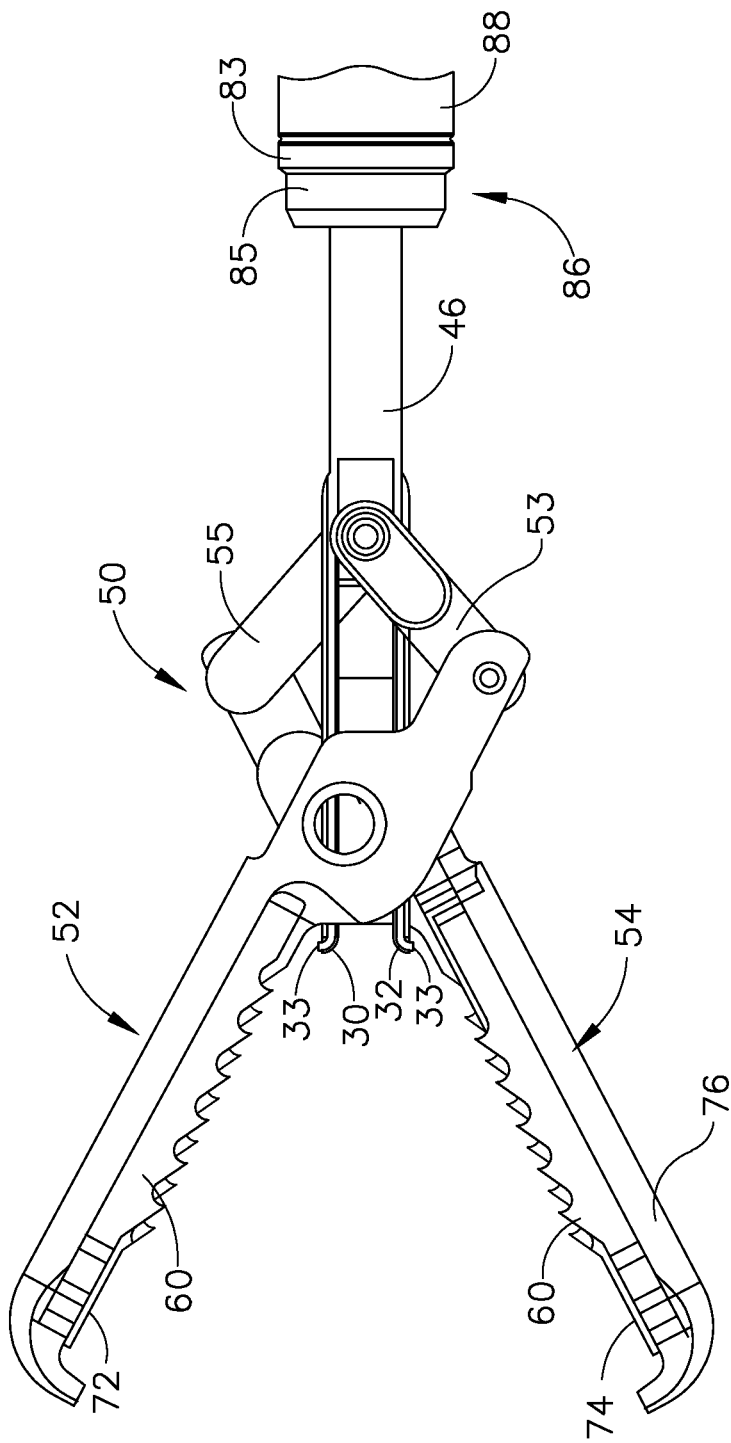
FIG. 9 is a left elevational view of the end effector of FIG. 3 with a clevis removed.
Figure 10:
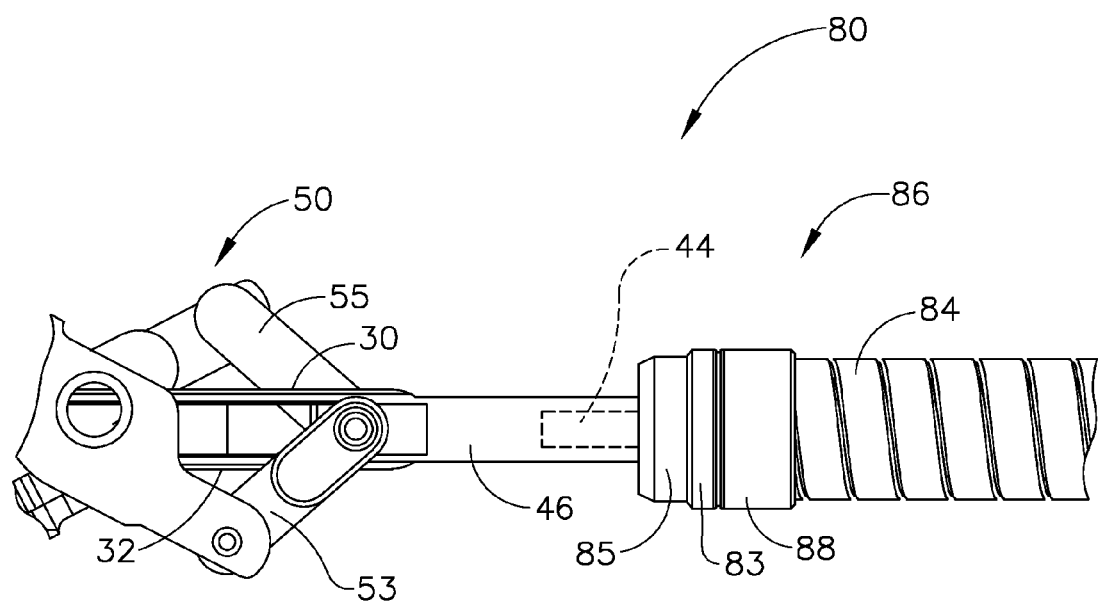
FIG. 10 is a left elevational view of a coupling between the end effector and the shaft assembly of the surgical instrument of FIG. 3.
Figure 11:
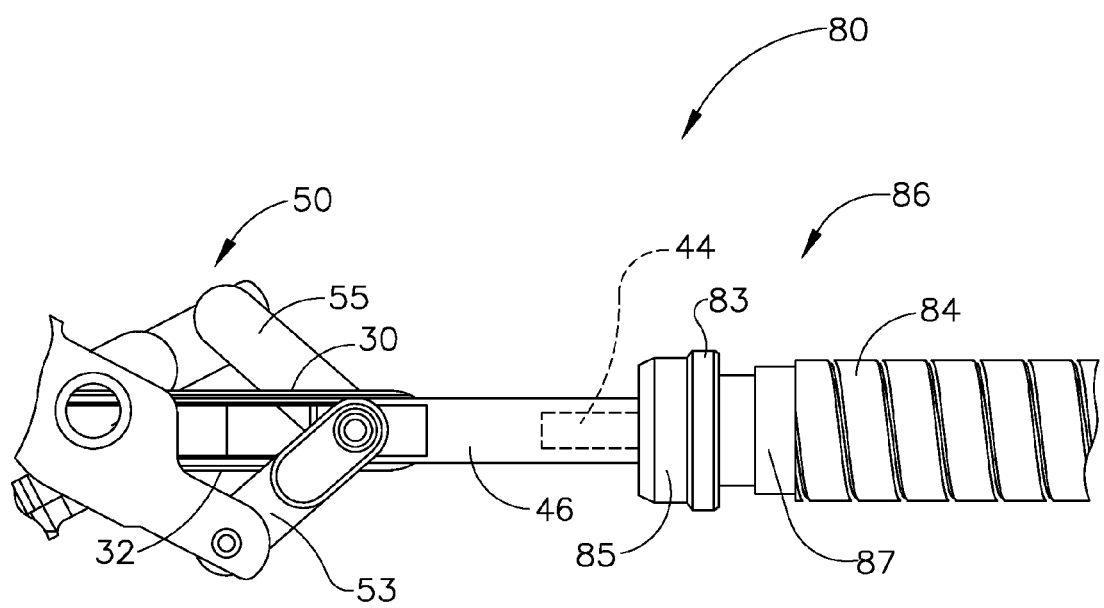
FIG. 11 is a left elevational view of the coupling of FIG. 10 with additional components removed.

Further to the above, in at least one embodiment, conductor 30, including contact end 33, can remain stationary, or at least substantially stationary, when first electrode 72 is moved between first and second positions as described above and, as a result, conductor 30 does not have to be bent or stretched to accommodate the movement of first electrode 72. In various circumstances, as a result, the likelihood that conductor 30 may break or become otherwise damaged can be reduced. As illustrated in FIGS. 5 and 6, surgical instrument 20 can include one or more additional electrodes which can be selectively placed in electrical communication with a conductor associated therewith. In at least one embodiment, similar to the above, second electrode 74 can be placed in electrical communication with second conductor 32 when jaw member 54 is in a first position and can be placed out of electrical communication with second conductor 32 when jaw member 54 is in a second position, for example. Although not illustrated, surgical instrument 20 can include one or more stationary jaws and electrodes which do not move relative to a corresponding conductor. In such embodiments, the conductor may be attached to the stationary electrode, for example.

In various embodiments, first electrode 72 and first conductor 30 may be coupled to the positive terminal of generator 38 and second electrode 74 and second conductor 32 may be coupled to the negative terminal. In other various embodiments, this arrangement may be reversed. In either event, the switches described above, including foot pedal 40 (FIG. 2), may be placed intermediate, or in series between, the positive terminal and the electrode coupled thereto. In such embodiments, the switch may prevent current from flowing from the generator to this electrode until the switch is actuated. Absent such a switch, current could flow through the circuit comprising first conductor 30, second conductor 32, first electrode 72, and second electrode 74 when the electrodes are placed in electrical communication with the conductors. In these embodiments, current could be immediately transferred to the electrodes, and the soft tissue positioned therebetween, when jaw members 52 and 54 are moved into their closed, or at least substantially closed, positions. While such embodiments can be useful, various surgical techniques may require that the electrodes be manipulated or repositioned on the soft tissue after the jaw members have been closed thereon. In such embodiments, the jaw members could be closed onto the soft tissue and the current could be delivered to the electrodes when a switch is activated as described above.

Figure 4:
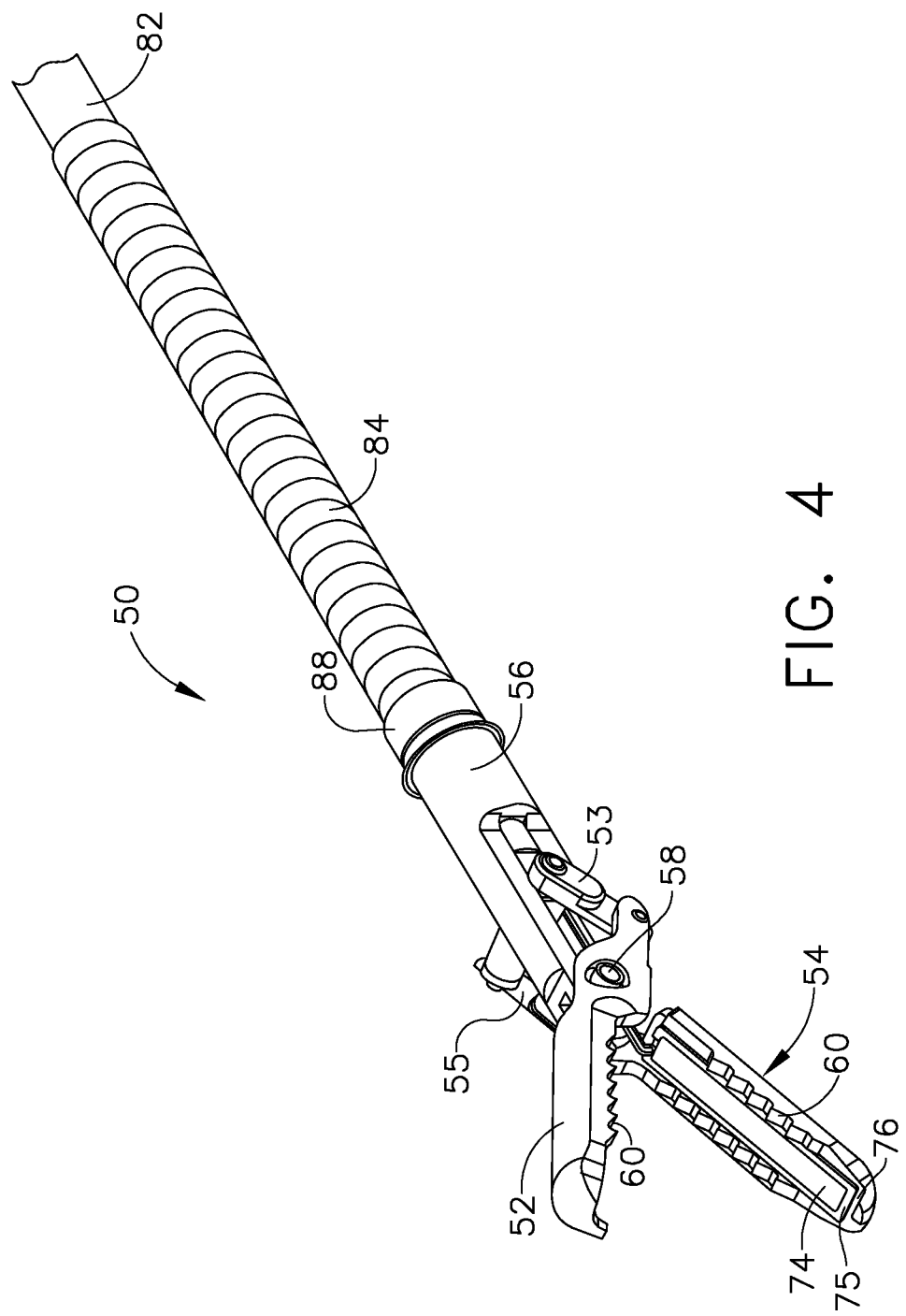
FIG. 4 is a perspective view of the end effector of FIG. 3.
Figure 12:
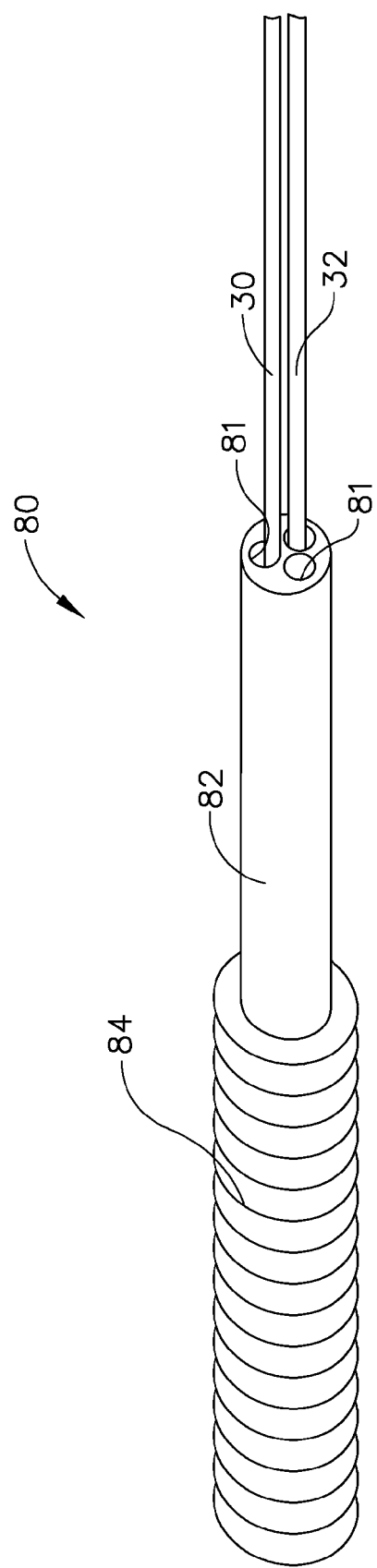
FIG. 12 is a perspective view of the shaft assembly of the surgical instrument of FIG. 3.

In various embodiments, referring to FIGS. 4 and 5, each jaw member 52 and 54 can further include an insulator 75 which can be configured to prevent current from flowing from electrodes 72 and 74, respectively, to the other portions of the jaw members. More particularly, absent an insulator 75 positioned intermediate second electrode 74 and outer portion 76 of jaw 54, for example, the current may flow between electrode 74 to outer portion 76 and then flow into adjacent tissue which is not the targeted tissue. In at least one embodiment, insulator 75 may be at least partially comprised of a ceramic material, for example. In various embodiments, conductors 30 and 32 can be comprised of insulated wires. For example, each conductor can include an inner core comprised, of copper, brass, and/or aluminum, for example, and an outer jacket, or sheath, which can cover the core, wherein the jacket can be comprised of PVC or any other suitable polymer, for example. In various embodiments, electrodes 72 and 74 can be comprised of any suitable conductive material such as gold plated stainless steel, for example. In various embodiments, referring to FIG. 12, elongate member 82 can include at least one aperture, or lumen, 81 extending therethrough which can be configured to receive and protect conductors, or wires, 30 and 32 extending between end effector 50 and hand piece 24 as described above. In various embodiments, a lumen 81 can be configured to receive actuator 44 which, as described above, is operably engaged with hand piece 24 and end effector 50.

In various embodiments, an electrode can be formed having a substantially flat paddle-like shape, and/or any other suitable shape. In such embodiments, as described above, the electrode can include a flat surface which can be configured to abut contact end 33 of a conductor. In at least one embodiment, the inner core of the conductor can be configured to touch a portion of this flat surface and place the electrode and the conductor in electrical communication. In various other embodiments, although not illustrated, the electrode can include an aperture, or receptacle, which can be configured to receive contact end 33 therein, for example. In at least one embodiment, contact end 33 can be configured to abut a sidewall of the receptacle or it can be configured to fit snugly therein. In either event, the engagement between the receptacle and contact 33 can prevent, or at least reduce the possibility of, relative movement between the conductor and the electrode when the jaw member is in its closed position. Such relative movement could cause intermittencies in the current flowing therebetween which could affect the reliability of the surgical instrument. In various embodiments, contact end 33 can comprise an electrical contact which is soldered onto, or otherwise attached to, the end of the inner core of the conductor. Such electrical contacts can be configured such that they fit snugly within the receptacles in the electrodes and may require a force to remove them therefrom.

In various embodiments, a bipolar forceps having two or more electrodes can be utilized to seal a vessel, such as a blood vessel, for example. In at least one embodiment, the electrodes can be positioned against, or adjacent to, the vessel and energy can be supplied to the electrodes. In various circumstances, the energy can be sufficient to at least substantially seal the vessel such that blood does not substantially flow therethrough. In at least one surgical technique, the bipolar forceps can be used to thermally seal the vessel in two locations such that the vessel can be incised, or transected, at a location positioned intermediate the two sealed locations. In various embodiments, the bipolar forceps can include a cutting element which can be configured to incise the vessel. Such bipolar forceps can reduce the complexity of various surgical techniques by allowing a surgeon to seal and transect soft tissue with a single surgical instrument as opposed to using at least two surgical instruments which were previously required.

Figure 15:
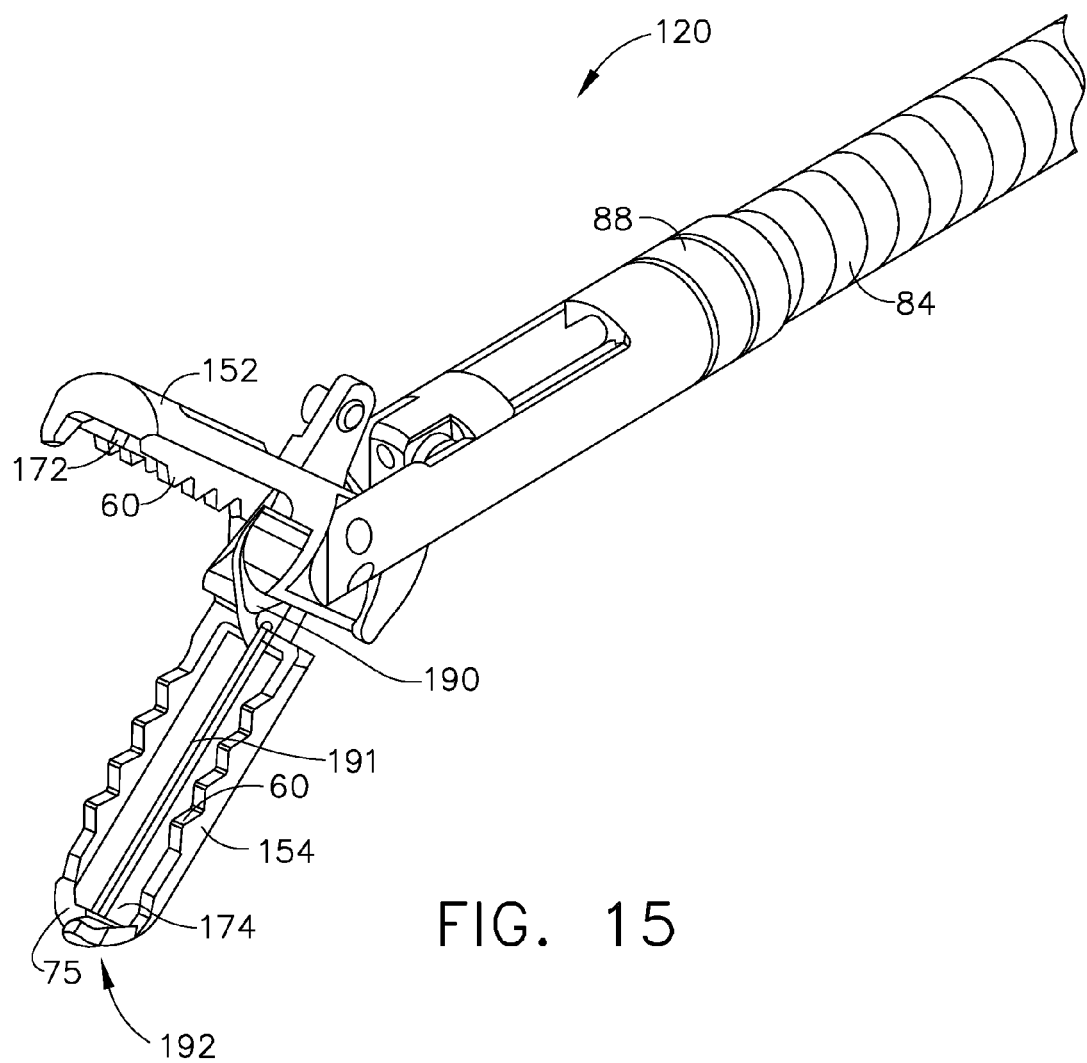
FIG. 15 is a perspective view of an end effector of a surgical instrument having a cutting element in accordance with an embodiment of the present invention.

Referring to FIG. 15, surgical instrument 120 can include first jaw member 152 and second jaw member 154 wherein, similar to the above, first jaw member 152 can include first electrode 172 and, in addition, second jaw member 154 can include second electrode 174. In at least one embodiment, surgical instrument 120 can further include cutting element 190, wherein cutting element 190 can be configured to incise soft tissue, for example, positioned intermediate jaw members 152 and 154. In various embodiments, cutting element 190 can be configured to be moved relative to jaw members 152 and 154 and/or electrodes 172 and 174. More particularly, in at least one embodiment, cutting element 190 can be moved between a first, or proximal, position, as illustrated in FIG. 15, to a second, or distal, position, within distal end 192. In various alternative embodiments, the cutting element can be moved from a distal position to a proximal position to incise the soft tissue, for example. In either event, in at least one embodiment, cutting element 190 can include a sharp, or knife, edge configured to incise the soft tissue, for example. In various embodiments, second electrode 174 can include slot 191 which can be configured to slidably receive cutting element 190 and guide it along a predetermined path. In at least one embodiment, as illustrated in FIG. 15, the predetermined path can be linear or at least substantially linear. In other various embodiments, the predetermined path can be curved and/or curvilinear. In any event, in at least one embodiment, first electrode 172 can include a slot therein which can also be configured to slidably receive and guide cutting element 190.

Figure 16:
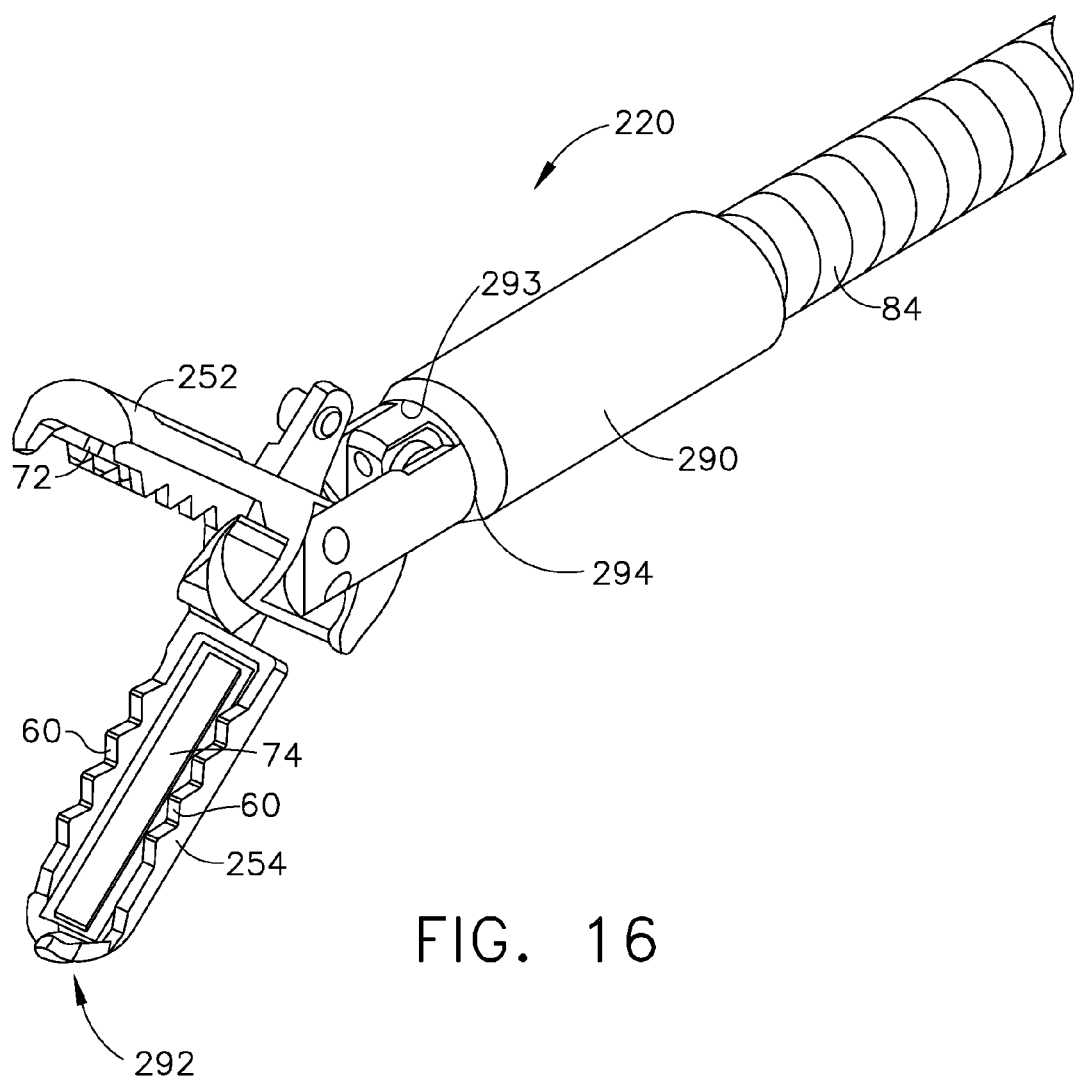
FIG. 16 is a perspective view of an end effector of a surgical instrument having a cutting element in accordance with an alternative embodiment of the present invention.

In various embodiments, referring to FIG. 16, surgical instrument 220 can include first jaw member 252 and second jaw member 254 where, similar to the above, jaw members 252 and 254 can be positioned relative to a vessel, for example, such that electrodes within the jaw members can be utilized to cauterize or seal the vessel. In at least one embodiment, surgical instrument 220 can further include cutting element, or cutting barrel, 290 movably attached thereto wherein cutting barrel 290 can be moved between first and second positions similar to the above. In use, jaw members 252 and 254 can be used to at least partially clamp the vessel therebetween such that cutting barrel 290 can be slid over the at least partially closed jaws. In other various embodiments, cutting barrel 290 can be slid against jaw members 252 and 254 in order to push them into an at least partially closed position. In either event, in at least one embodiment, cutting barrel 290 can include aperture 293 extending therethrough which can be configured to receive at least a portion of jaws 252 and 254 as cutting barrel 290 is moved toward distal end 292. In at least one surgical technique, a vessel can be thermally sealed at two locations by electrodes 72 and 74 as described above. Thereafter, jaws 252 and 254 can be positioned intermediate the two sealed locations, jaws 252 and 254 can be at least partially closed onto the vessel, and cutting barrel 290 can be slid distally until cutting edge 294 contacts and incises the vessel.

Figure 17:
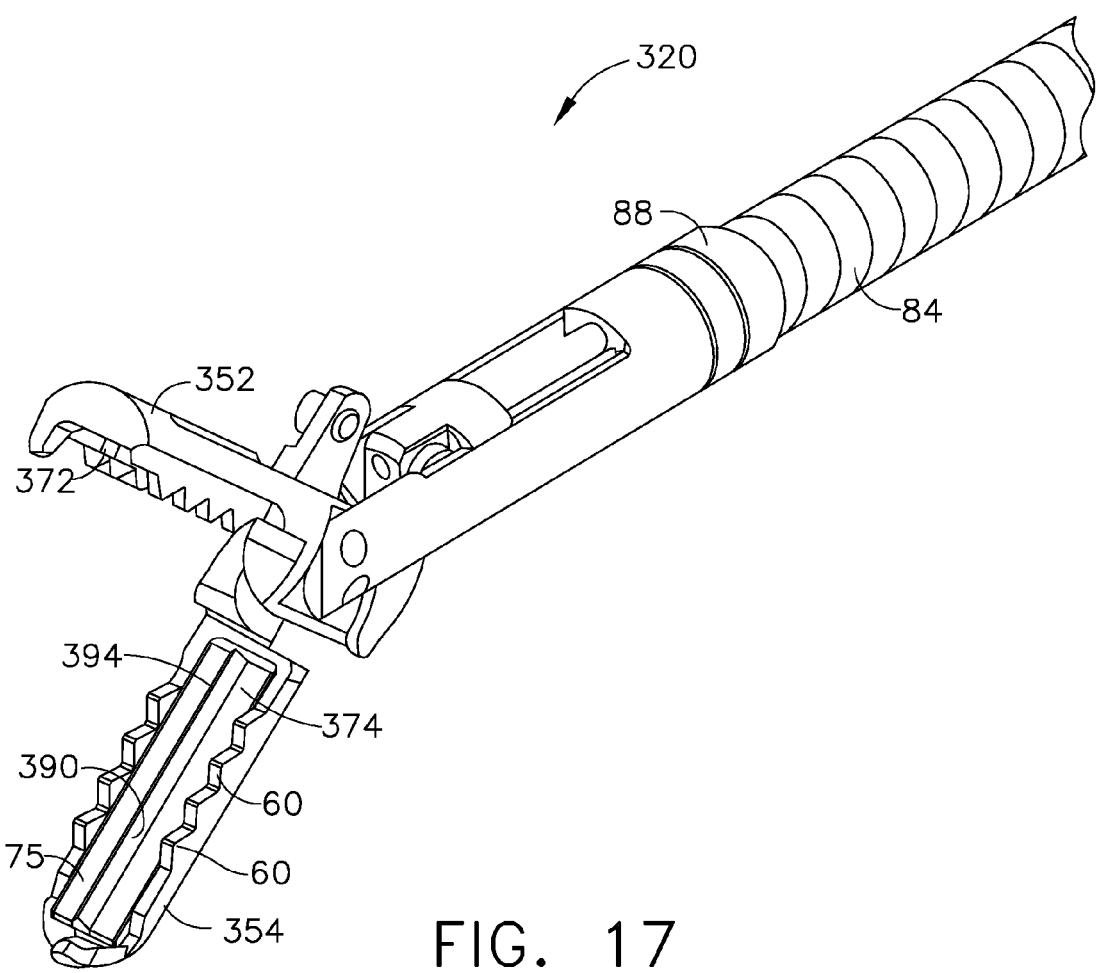
FIG. 17 is a perspective view of an end effector of a surgical instrument having a cutting element extending from an electrode in accordance with an alternative embodiment of the present invention.
Figure 18:
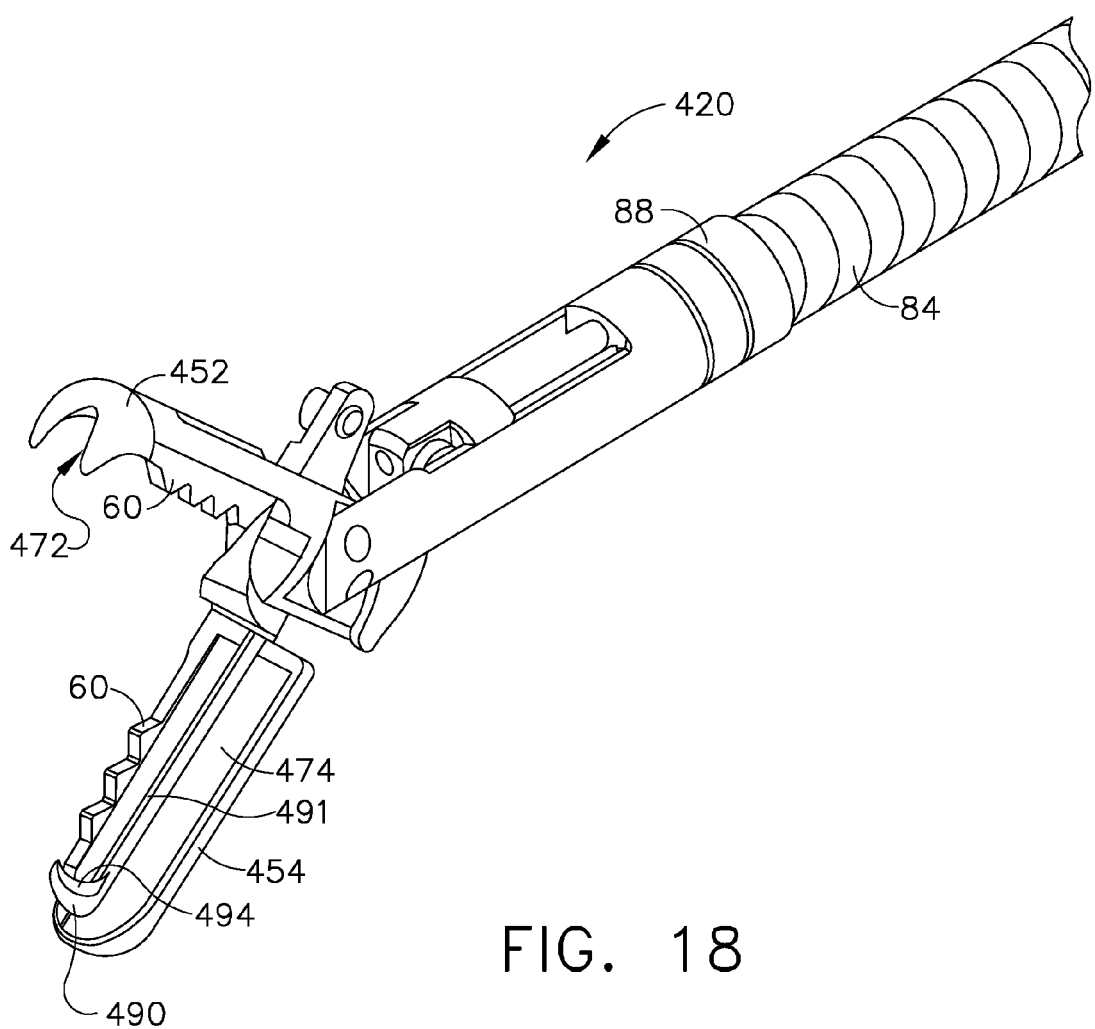
FIG. 18 is a perspective view of an end effector of a surgical instrument having a cutting element configured to be energized in accordance with an alternative embodiment of the present invention.

In various embodiments, referring to FIG. 17, surgical instrument 320 can include first jaw member 352 and second jaw member 354 wherein, similar to the above, first jaw member 352 can include first electrode 372 and, in addition, second jaw member 354 can include second electrode 374. In at least one embodiment, at least one of first electrode 372 and second electrode 374 can include at least one cutting element 390 extending therefrom. In various embodiments, cutting element 390 can comprise a projection, or 'high point', having at least one cutting edge 394 configured to incise, or otherwise treat, soft tissue, such as a vessel, for example, when jaw members 352 and 354 are closed onto the soft tissue. In at least one embodiment, cutting edge 394 can be sharp enough to incise the soft tissue when a closing force is applied to jaw members 352 and 354. In various embodiments, energy can be applied to the cutting element via the electrode in order for the cutting element to transect the tissue. In such embodiments, the density of the energy within the electrode can be concentrated at the projection, or high point, of the electrode owing to the reduced surface area of the electrode in contact with the soft tissue. In various embodiments, referring to FIG. 18, surgical instrument 420 can include first jaw member 452 and second jaw member 454 wherein, similar to the above, first jaw member 452 can include first electrode 472 and, in addition, second jaw member 454 can include second electrode 474. In at least one embodiment, surgical instrument 420 can further include cutting element 490, wherein cutting element 490 can be configured to incise soft tissue, for example, positioned intermediate jaw members 452 and 454. In various embodiments, similar to the above, cutting element 490 can be configured to be moved relative to jaw members 452 and 454 and/or electrodes 472 and 474 along a predetermined path. In at least one embodiment, at least one of electrodes 472 and 474 and/or jaw members 452 and 454 can include a slot 491 therein which can be configured to slidably receive cutting element 490.

Figure 19:
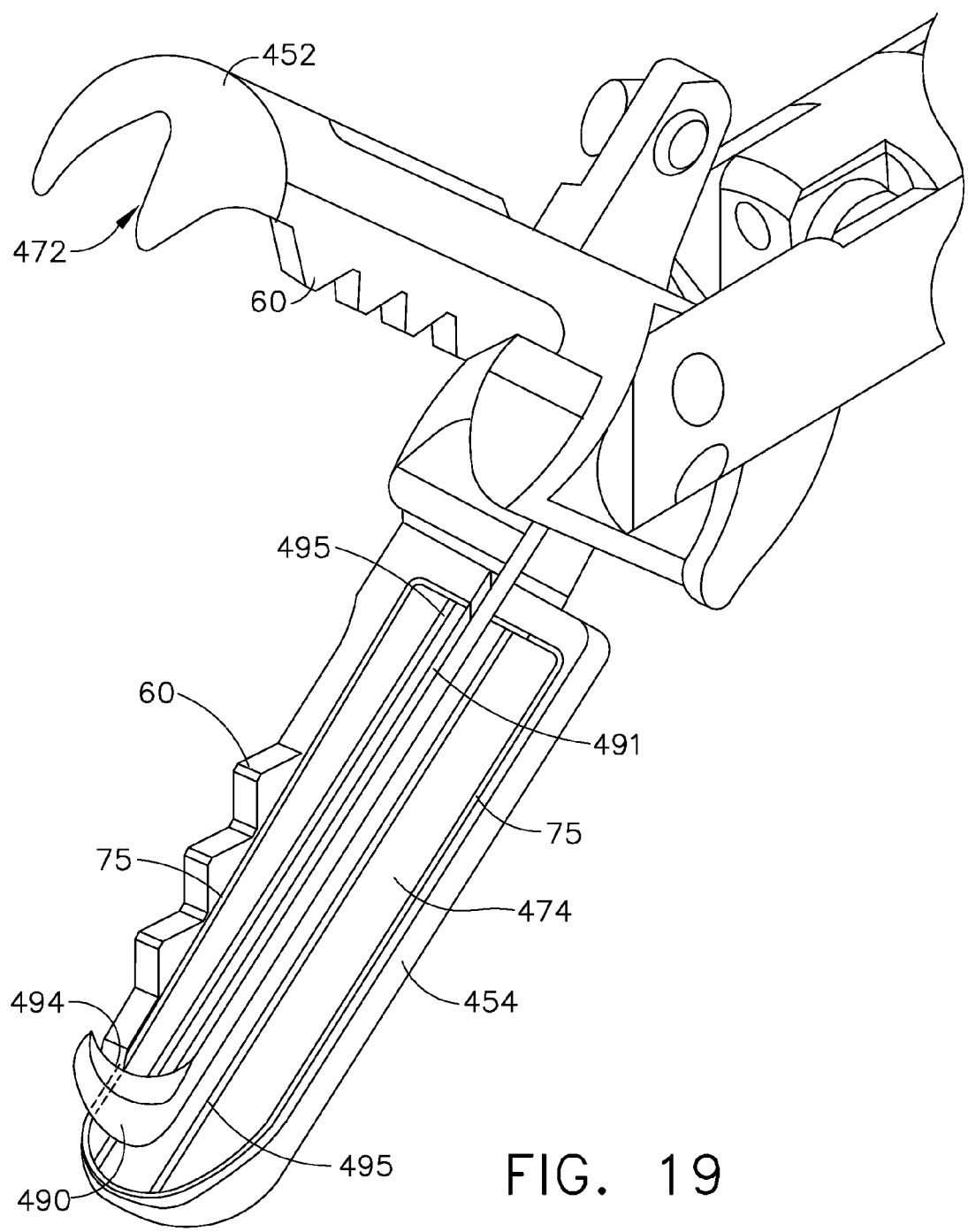
FIG. 19 is a detail view of an insulator positioned intermediate an electrode and the cutting element of FIG. 18.
Figure 20:
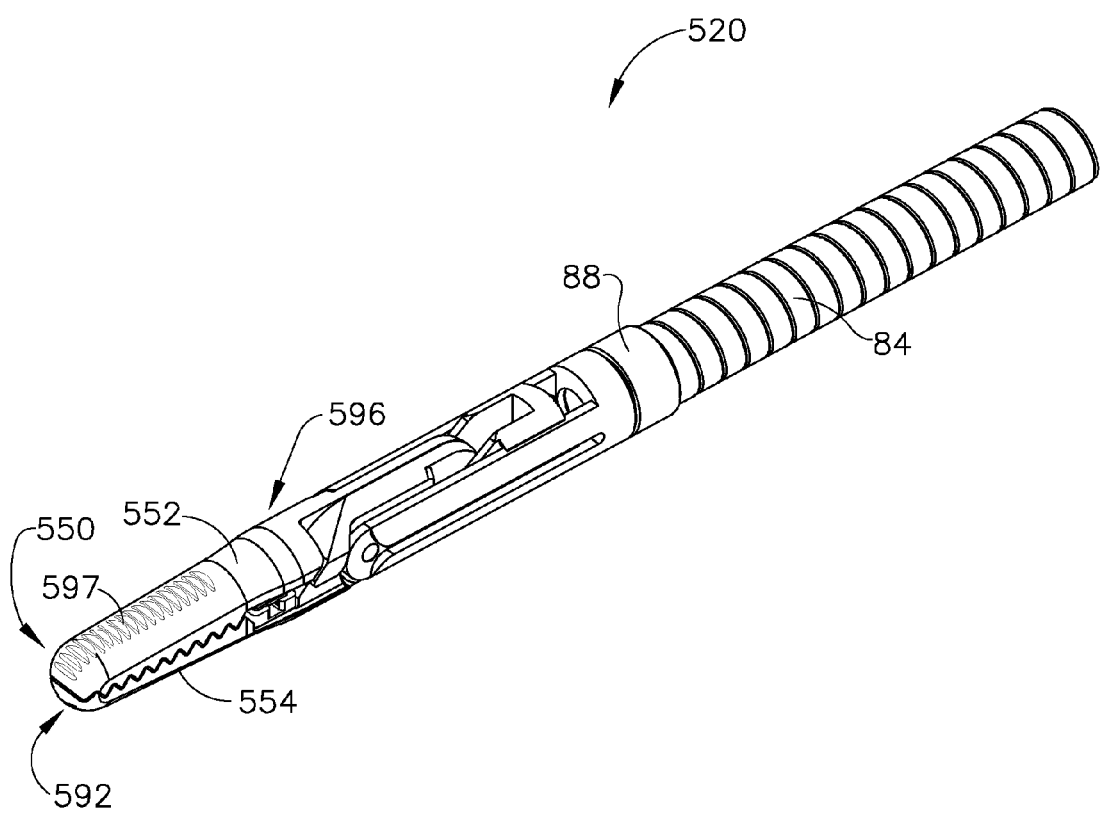
FIG. 20 is a perspective view of an end effector of a surgical instrument having a tapered profile in accordance with an alternative embodiment of the present invention.

In various embodiments, cutting element 490 can be energized to incise, or otherwise treat, the soft tissue positioned intermediate jaw members 452 and 454. In at least one embodiment, cutting element 490 can be placed in electrical communication with a monopolar output of an electrosurgical generator such that current can flow from the generator into the soft tissue via cutting element 490. In order to complete the monopolar circuit, a return electrode, or pad, can be placed in contact with the patient's body and can be placed in electrical communication with the generator and/or another suitable ground. In other various embodiments, although not illustrated, surgical instrument 420 can include a return circuit for the electrical current. In either event, referring to FIG. 19, jaw member 454 can further include insulator 495 positioned intermediate cutting element 490 and second electrode 474 to electrically insulate cutting element 490 from electrode 474. In at least one embodiment, insulator 495 can define slot 491 such that cutting element 490 is at least substantially surrounded by insulator 495. Insulator 495 can be comprised of any suitable material such as a ceramic material, for example.

In at least one surgical technique, bipolar electrodes 472 and 474 can be utilized to at least partially seal a vessel as described above. Thereafter, electrodes 472 and 474 can be positioned intermediate the two seals and cutting element 490 can be slid until it touches the vessel. To incise the vessel, the surgeon can operate a switch, for example, to allow current to flow to cutting member 490. In various circumstances, depending on the frequency and voltage of the current, for example, cutting element 490 configured to cut and/or coagulate the soft tissue. In either event, surgical instrument 420 can include a switch, for example, which can be configured to place surgical instrument 420 in a plurality of operating modes. In at least one embodiment, the switch can place instrument 420 in a first operating mode in which electrical energy is supplied to electrodes 472 and 474, but not to cutting element 490. The switch can also place instrument 420 in a second operating mode in which electrical energy is supplied to cutting element 490, but not electrodes 472 and 474. In such embodiments, the possibility of energy being unintentionally transmitted to the targeted soft tissue, or the surrounding soft tissue, can be reduced. In at least one embodiment, cutting element 490 can further include cutting edge 494 which can be configured to incise, or bluntly dissect, the soft tissue. Such embodiments can provide a surgeon with several options for incising soft tissue.

In various embodiments, referring to FIGS. 20-24, a bipolar forceps can include first and second jaw members wherein at least one of the jaw members can include a substantially tapered profile. More particularly, in at least one embodiment, surgical instrument 520 can include end effector 550 having proximal end 596 and distal end 592 where end effector 550 can be tapered between proximal end 596 and distal end 592. In various embodiments, proximal end 596 can define a first perimeter and distal end 592 can define a second perimeter wherein the first perimeter can be larger than the second perimeter. Similarly, proximal end 596 can include a cross-section defined by a first diameter and distal end 592 can include a cross-section defined by a second diameter wherein the first diameter can be larger than the second diameter. Although embodiments where ends 592 and 596 have circular cross-sections are envisioned, other embodiments having non-circular cross-sections are also possible. In either event, in various embodiments, a 'tapered' end effector can include a cross-section which becomes gradually smaller between proximal end 596 and distal end 592. Such a taper can be constant along the length of end effector 550 or the taper can include at least two sections having different tapered profiles. In either event, as described in greater detail below, a bipolar forceps having a tapered end effector can be useful in various surgical techniques.

In at least one surgical technique, distal end 592 can be positioned intermediate a vessel and soft tissue surrounding the vessel in order to separate the vessel from the soft tissue. More particularly, end effector 550 can be positioned intermediate the vessel and the soft tissue in a substantially closed position and can be opened such that jaw members 552 and 554 contact the vessel and soft tissue and push them away from each other. In various circumstances, end effector 550 can be opened and closed several times to enlarge a hole between the vessel and soft tissue such that the vessel and the soft tissue can be further separated. In various embodiments, again referring to FIGS. 20-24, at least one of jaw members 552 and 554 can further include ridges, teeth, and/or a textured outer surface configured to grip the soft tissue and/or vessel. In at least one embodiment, jaw member 552, for example, can include ridges 597 extending therefrom along a line defined between distal end 592 and proximal end 596. In various embodiments, ridges 597 can be configured such that, when the jaw members contact the soft tissue and/or vessel as described above, the jaw members can pull the soft tissue and vessel therewith. In effect, ridges 597, for example, can prevent, or at least inhibit, jaw members 552 and 554 from sliding past the soft tissue and/or vessel when the jaw members are opened.

Figure 21:
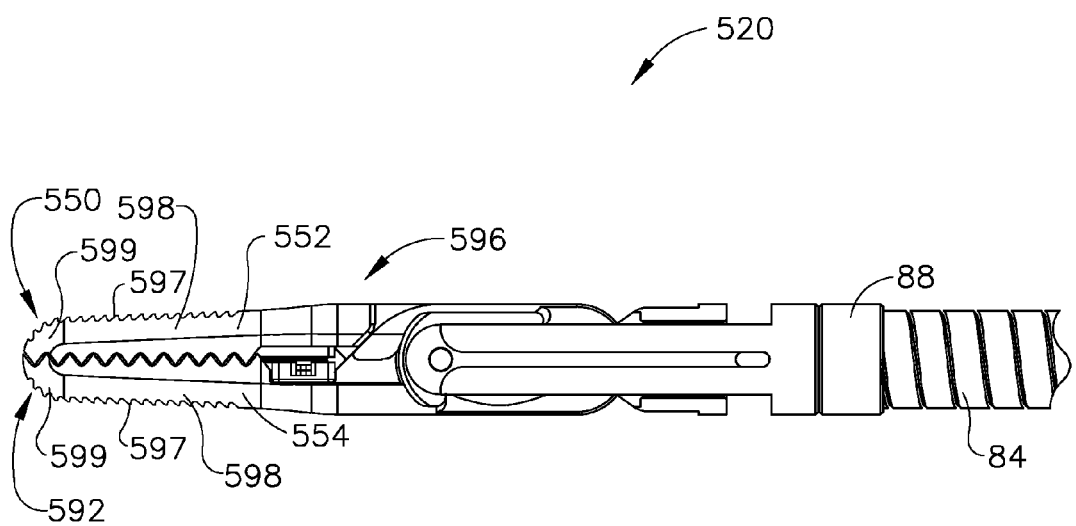
FIG. 21 is an elevational view of the end effector of FIG. 20.
Figure 22:
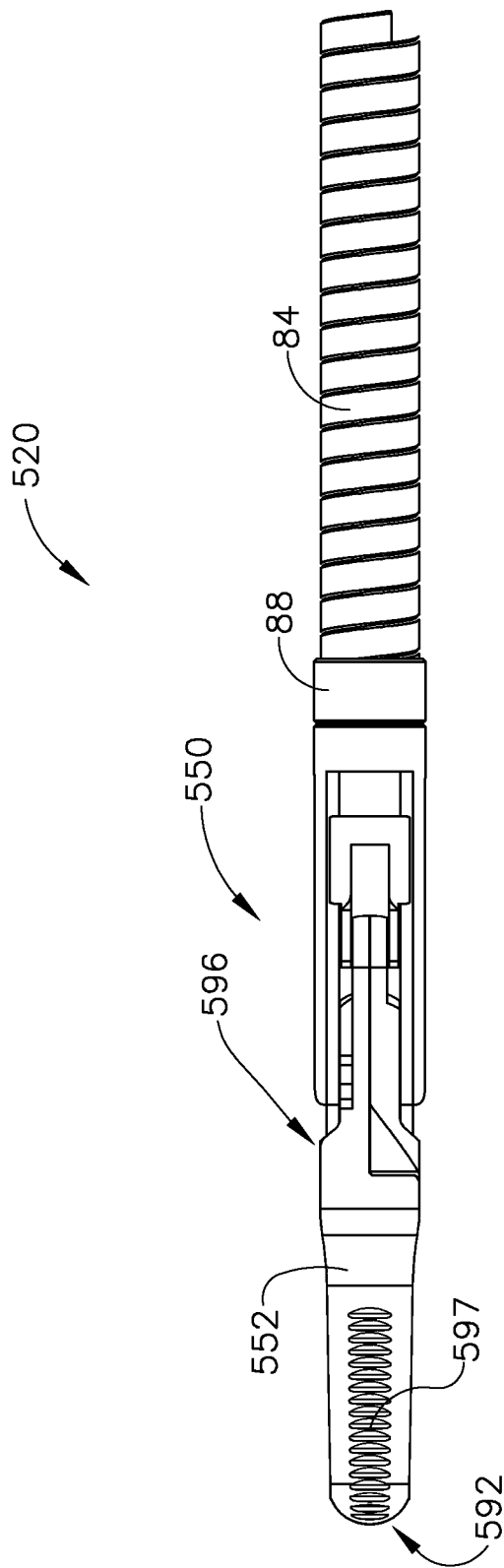
FIG. 22 is a top view of the end effector of FIG. 20.
Figure 23:
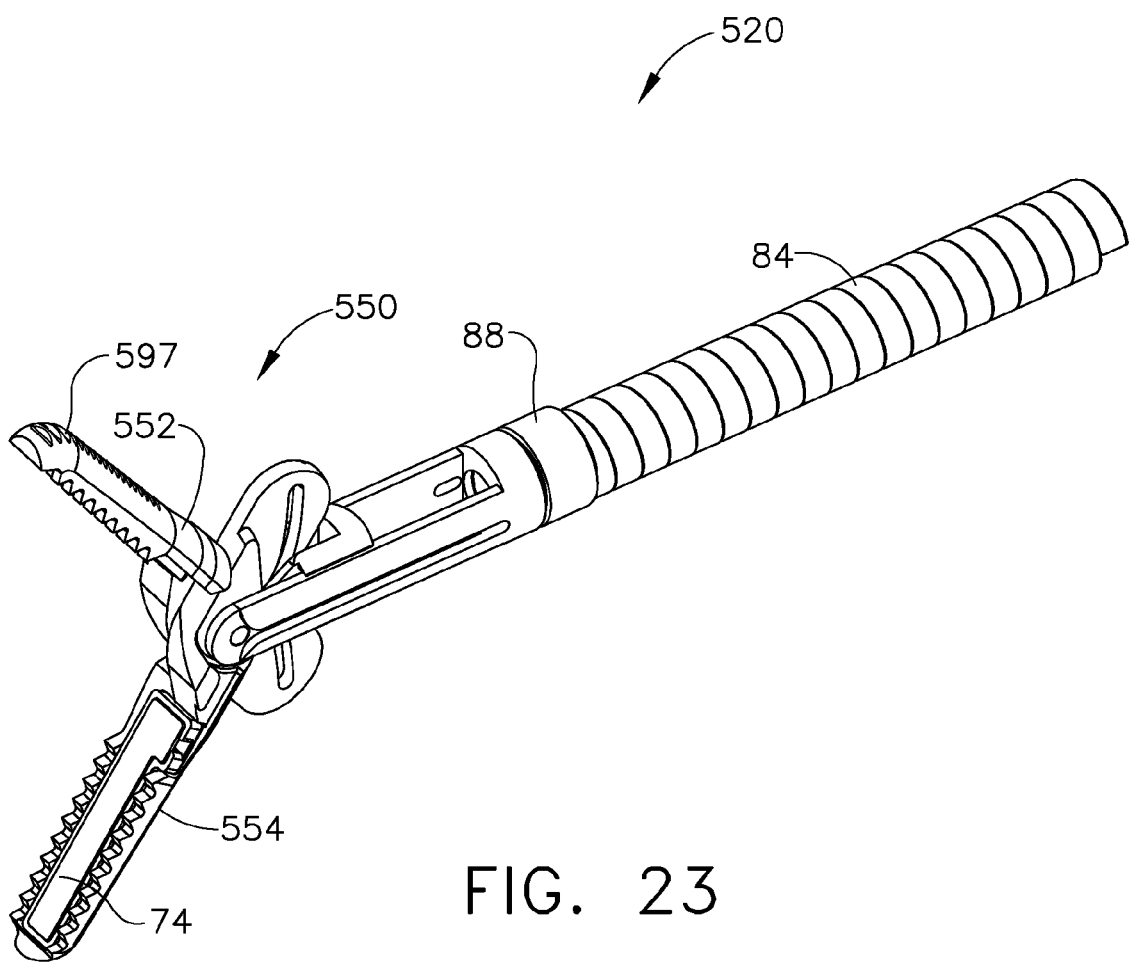
FIG. 23 is a perspective view of the end effector of FIG. 20 in an open configuration.
Figure 24:
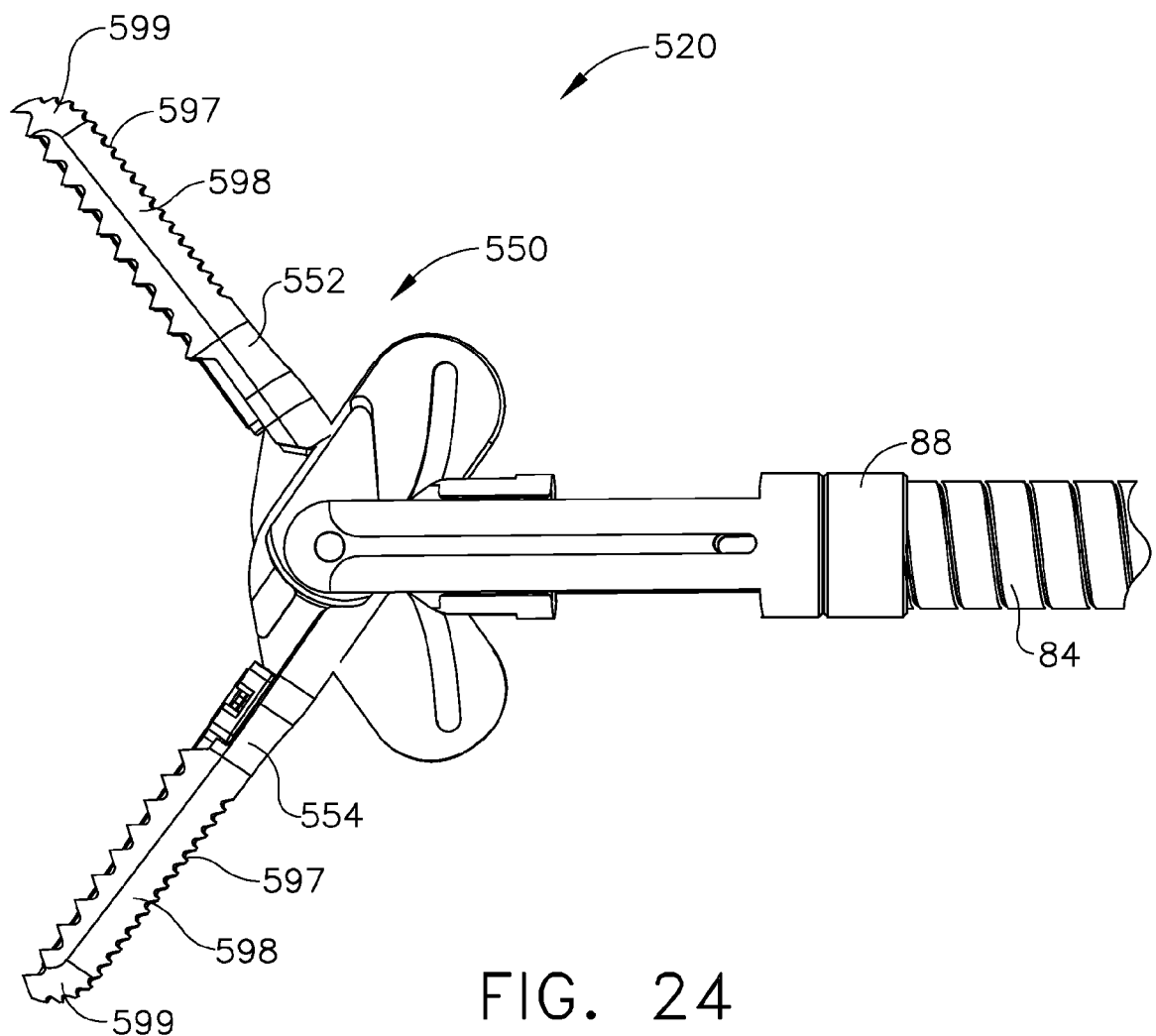
FIG. 24 is an elevational view of the end effector of FIG. 20 in the configuration of FIG. 23.

In various embodiments, referring to FIGS. 21 and 24, jaw member 552, for example, can include tapered portion 598 and bullet nose portion 599. In at least one embodiment, both tapered portion 598 and bullet nose portion 599 can include ridges 597, for example, extending therefrom. In such embodiments, bullet nose portion 599 can be especially configured to be burrowed between the vessel and the surrounding soft tissue, as described above, as ridges 597 extending from bullet nose portion 599 can facilitate the creation of a hole in the connective tissue intermediate the vessel and the soft tissue. In addition to or in lieu of the above, the outer surfaces of jaw members 552 and 554 can include an outer surface having a rough texture which can also be configured to prevent, or at least reduce, slipping between the jaw members and the soft tissue and/or vessel. In at least one embodiment, the outer surface of jaw members 552 and 554 can be abraded. In various embodiments, a rough coating can be sprayed onto the jaw members. In either event, once the vessel has been at least partially separated from the soft tissue, one of jaw members 552 and 554 can be positioned intermediate the vessel and the soft tissue and the other of jaw members 552 and 554 can be positioned on the opposite side of the vessel. Thereafter, the electrodes positioned within jaw members 552 and 554 can be utilized to thermally seal the vessel as described above.

In at least one embodiment, the first and second electrodes can be adapted to receive an irreversible electroporation (IRE) waveform from an IRE generator. In another embodiment, the first and second electrodes can be adapted to receive a radio frequency (RF) waveform from an RF generator. In various embodiments, the electrical waveform generator may be a conventional, bipolar/monopolar electrosurgical IRE generator such as one of many models commercially available, including Model Number ECM 830, available from BTX Molecular Delivery Systems Boston, Mass. The IRE generator can generate electrical waveforms having predetermined frequency, amplitude, and pulse width. In various circumstances, the application of these electrical waveforms to the cell membranes of the diseased tissue causes the diseased cells to die. Thus, the IRE electrical waveforms may be applied to the cell membranes of diseased tissue in the tissue treatment region in order to kill the diseased cells and ablate the diseased tissue. IRE electrical waveforms suitable to destroy the cells of diseased tissues are generally in the form of direct current (DC) electrical pulses delivered at a frequency in the range of 1-20 Hz, amplitude in the range of 100-1000 VDC, and pulse width in the range of 0.01-100 ms. For example, an electrical waveform having amplitude of 500 VDC and pulse duration of 20 ms may be delivered at a pulse repetition rate or frequency of 10 HZ to destroy a reasonably large volume of diseased tissue. Unlike RF ablation systems which require high powers and energy input into the tissue to heat and destroy, IRE requires very little energy input into the tissue, rather the destruction of the tissue is caused by high electric fields. It has been determined that in order to destroy living tissue, the electrical waveforms have to generate an electric field of at least 30,000V/m in the tissue treatment region. The embodiments, however, are not limited in this context.

In at least one embodiment, the electrical waveform generator may comprise a radio frequency (RF) waveform generator. The RF generator may be a conventional, bipolar/monopolar electrosurgical generator such as one of many models commercially available, including Model Number ICC 350, available from Erbe, GmbH. Either a bipolar mode or monopolar mode may be used. When using the bipolar mode with two electrodes, one electrode can be electrically connected to one bipolar polarity, and the other electrode can be electrically connected to the opposite bipolar polarity. If more than two electrodes are used, the polarity of the electrodes may be alternated so that any two adjacent electrodes have opposite polarities.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, various embodiments of the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the instrument is sterilized. This can be done by any number of ways known to those skilled in the art including beta or gamma radiation, ethylene oxide, steam.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains. Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument for treating soft tissue, comprising:

a flexible shaft;

a housing extending from said flexible shaft;
a conductor in electrical communication with an energy source, said conductor having a contact portion; and
a jaw rotatably connected to said housing, wherein said jaw is configured to be inserted through a working channel of an endoscope, wherein said jaw is selectively rotatable between a first position, an intermediate position, and a second position, wherein said intermediate position is between said first position and said second position, and wherein said jaw includes:
  an electrode, wherein said electrode is not in contact with said contact portion when said jaw is in said first position and when said jaw is in said intermediate position, and wherein said electrode is configured to contact said contact portion when said jaw is in said second position such that said electrode is in electrical communication with said conductor to transmit energy to the soft tissue.

2. The surgical instrument of claim 1, wherein said electrode comprises a first electrode, and wherein said surgical instrument further comprises:
  a second conductor comprising a second contact portion; and
  a second jaw comprising a second electrode, wherein said second electrode is operably configured to contact said second contact portion such that said second electrode is in electrical communication with said second conductor to transmit energy to said first electrode via the soft tissue.

3. A method for processing an instrument for surgery, the method comprising:
  obtaining the surgical instrument of claim 1;
  sterilizing the surgical instrument; and
  storing the surgical instrument in a sterile container.

4. A surgical instrument for treating soft tissue, comprising:
  a flexible shaft;
  a first jaw;
  a second jaw rotatably coupled to said first jaw, wherein said first and second jaws are configured to be inserted through a working channel of an endoscope, wherein said second jaw is selectively rotatable between a first position, an intermediate position, and a second position, and wherein said intermediate position is between said first position and said second position;
  a conductor in electrical communication with an energy source, said conductor having a contact portion; and
  an electrode, wherein said electrode is not in contact with said contact portion when said second jaw is in said first position and when said second jaw is in said intermediate position, and wherein said electrode is configured to contact said contact portion when said second jaw is in said second position such that said electrode is in electrical communication with said conductor to transmit energy to the soft tissue.

5. The surgical instrument of claim 4, wherein said electrode comprises a second electrode, and wherein said surgical instrument further comprises:
  a first conductor comprising a first contact portion; and
  a first electrode on said first jaw, wherein said first electrode is configured to operably contact said first contact portion such that said first electrode is in electrical communication with said first conductor to transmit energy to said second electrode via the soft tissue.

6. A method for processing an instrument for surgery, the method comprising:
  obtaining the surgical instrument of claim 4;
  sterilizing the surgical instrument; and
  storing the surgical instrument in a sterile container.

* * * * *